United States Patent
Langhans et al.

(10) Patent No.: US 8,835,124 B2
(45) Date of Patent: Sep. 16, 2014

(54) METHOD FOR TREATING CANCER WITH AGENTS THAT BIND PHOSPHORYLATED CDC27

(71) Applicant: The Nemours Foundation, Jacksonville, FL (US)

(72) Inventors: Sigrid Anne-Barbara Langhans, West Chester, PA (US); Seung Joon Lee, Bear, DE (US)

(73) Assignee: The Nemours Foundation, Jacksonville, FL (US)

( * ) Notice: Subject to any disclaimer, the term of this patent is extended or adjusted under 35 U.S.C. 154(b) by 0 days.

(21) Appl. No.: 13/667,328

(22) Filed: Nov. 2, 2012

(65) Prior Publication Data
US 2013/0116335 A1    May 9, 2013

Related U.S. Application Data

(60) Provisional application No. 61/555,782, filed on Nov. 4, 2011.

(51) Int. Cl.
*G01N 33/574* (2006.01)

(52) U.S. Cl.
USPC ........................................ 435/7.23

(58) Field of Classification Search
None
See application file for complete search history.

(56) References Cited

U.S. PATENT DOCUMENTS

| | | | |
|---|---|---|---|
| 7,566,548 B2 | 7/2009 | Green et al. | 435/7.71 |
| 2002/0028472 A1 | 3/2002 | Gmachl et al. | 435/7.21 |
| 2005/0014206 A1 | 1/2005 | Vodermaier et al. | 135/7.21 |
| 2005/0181360 A1 | 8/2005 | Bernards et al. | 435/6 |
| 2006/0057652 A1 | 3/2006 | Green et al. | 435/7.23 |

OTHER PUBLICATIONS

Grosstessner-Haint et al (Molecular & cellular Proteomics, 2011, 10.1074/mcp.M111.008540, 1-11; published online Aug. 21, 2011).*
Cheng et al (Anticancer Research, 2001, 21:2895-2900).*
Bernard, et al., "Curcumin Cross-links Cystic Fibrosis Transmembrane Conductance Regulator (CFTR) Polypeptides and Potentiates CFTR Channel Activity by Distinct Mechanisms", *Journal of Biological Chemistry*, vol. 284, No. 45, pp. 30754-30765, 2009.
Kimata, et al., "A Role for the Fizzy/Cdc20 Family of Protein in Activation of the APC/C Distinct from Substrate Recruitment", *Molecular Cell* 32, 576-583, 2008.
King, et al., "A 20S Complex Containing CDC27 and CDC16 Catalyzes the Mitosis-Specifi- Conjugation of Ubiquitin to Cyclin B", *Cell*, vol. 81, 279-288, 1995.
Kraft, et al., "Mitotic regulation of the human anaphase—promoting complex by phosphorylation", *The EMBO Journal*, vol. 22, No. 24, p. 6598-6609, 2003.
Lee, et al., Curcumin-induced HDAC inhibition and attenuation of medulloblastoma growth in vitro and in vivo, *BMC Cancer*, 11; 144, 2011.
Matyskiela, et al., "Analysis of activator-binding sites on the APC/C supports a cooperative substrate-binding mechanism", *Mol Cell.*, 34(1): 68-80, 2009.
Nasmyth, "Segregating, Sister Genomes: The Molecular Biology of Chromosome Separation", *Science*, vol. 297, No. 5581, pp. 559-565, 2002.
Peters, "The anaphase promoting complex/cyclosome: a machine designed to destroy", *Nature Reviews Molecular Cell Biology* 7, 644-656, 2006.
Rajasekaran, et al., "Prostate specific membrane antigen associates with anaphase promoting promoting complex and induces chromosomal instability", *Mol Cancer Ther.*, (7): 2142-2151, 2008.
Thornton, et al., "An architectural map of the anaphase-promoting complex", *Genes & Development* 20: 449-460, (2006).
Tugendreich, et al., "Linking yeast genetics to mammalian genomes: Identification and mapping of the human homnolog CDC27 via the expressed sequence tag (EST), data base", *Proc. Nati. Acad. Sci, USA*, vol. 90, pp. 10031-10035, 1993.
Yu, "Cdc20: A WD40 Activator for a Cell Cycle Degradation Machine", *Molecular Cell* 27, 2007.

* cited by examiner

*Primary Examiner* — Laura B Goddard
(74) *Attorney, Agent, or Firm* — Drinker Biddle & Reath LLP

(57) ABSTRACT

The presence of phosphorylated Cdc27 in cancer cells is utilized to identify patients likely to benefit from treatment with a chemotherapeutic agent that binds to, or binds to and crosslinks, phosphorylated Cdc27, e.g., curcumin, or to determine whether patients undergoing such treatment will continue to respond effectively. Candidate compounds are screened for anticancer effect by testing the ability to bind to or crosslink phosphorylated Cdc27.

21 Claims, 9 Drawing Sheets

METHOD FOR TREATING CANCER WITH AGENTS THAT BIND PHOSPHORYLATED CDC27

CROSS-REFERENCE TO RELATED APPLICATION

This application claims the benefit of U.S. Provisional Application No. 61/555,782, filed Nov. 4, 2011, the entire disclosure of which is incorporated herein by reference.

FIELD OF THE INVENTION

The invention relates to methods for identification of candidate compounds that modulate apoptosis of cancer cells and provide therapeutic agents for the treatment of cancer, and methods for predicting the effectiveness of anticancer therapy with selected therapeutic agents.

BACKGROUND OF THE INVENTION

Curcumin

Curcumin is a component of turmeric, the yellow spice derived from roots of the plant Curcuma longa, and is also known as diferuloylmethane, or (E,E)-1,7-bis(4-hydroxy-3-methoxyphenyl)-1,6-heptadiene-3,5-dion. Curcumin has the structure:

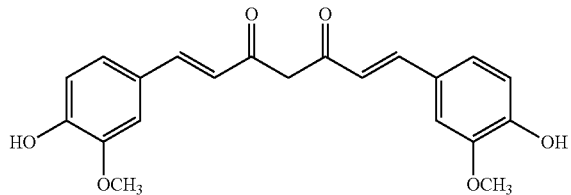 [SMILES: COc1cc(/C=C/C(=O)CC(=O)/C=C/c2ccc(O)c(OC)c2)ccc1O]

There are several curcumin analogs that include the natural curcuminoids demethoxycurcumin and bisdemethoxycurcumin, and synthesized analogs such as curcumin derivatives. Curcumin derivatives retain the basic structural features of curcumin but include modifications such as acetylation, alkylation, glycosylation, and amino acetylation of the phenolic hydroxyl group, demethylation of the methoxy groups, or acetylation, alkylation and substitution of the reactive methylene group of the linker, among other modifications. Curcumin analogues are all other compounds with structural analogy to curcumin and include natural compounds such as ferulic acid, cinnamic acid, caffeic acid, capsaicin, and gingerol. Metal complexes of curcumin have been described as well. To increase the bioavailability of curcumin, various drug-delivery systems have been developed, ranging from polymeric and solid lipid nanoparticles to liposomal formulations, and microparticle and microemulsion formulations.

Curcumin has potent anti-cancer properties which are chemopreventive and chemotherapeutic. No discernible side effects have been reported in phase I and II clinical trials in the U.S. Studies in tumor cells and animal tumor models have shown that curcumin can inhibit proliferation in various cancers either alone or in combination with other chemotherapeutic agents. Due to its ability to cross the brain blood-barrier, an impediment to drug delivery of many chemotherapeutics to the brain, curcumin can inhibit medulloblastoma growth in a medulloblastoma in vivo model (Lee et al., 2011, BMC Cancer 11:144). Other cancers in which curcumin has been proposed to be effective include, but are not limited to, hematological cancers (acute lymphoblastic leukemia ALL, acute T cell leukemia ATL, acute myelogenous leukemia AML, promyelocytic leukemia, erythromyeloblastoid leukemia) and lymphomas (Burkitt's lymphoma, Hodgkin's lymphoma, Non-Hodgkin's lymphoma, follicular lymphoma, primary effusion lymphoma), multiple myeloma, gastrointestinal cancers (esophagus, intestine, liver, pancreas, colon, rectum), bladder, kidney, prostate, breast, cervix, ovary, lung melanoma, and brain tumors. Although curcumin has been identified as one of the major natural agents that inhibit tumor growth, it is not known why curcumin preferentially kills cancer cells. No reliable marker exists that could predict which tumors will respond to curcumin treatment.

Curcumin can arrest cell-cycle progression and induce apoptosis in various cancer cells (Sa and Das, 2008, Cell Division 3:14). Curcumin induces G2/M arrest and apoptosis in medulloblastoma cells (Bangaru et al., 2010, Anticancer Research 30:499-504; Elamin et al., 2010, Molecular Carcinogenesis 49:302-314; Lee et al., 2011, BMC Cancer 11:144). However, the molecular mechanism how curcumin induces cell cycle arrest at G2/M remains elusive.

Curcumin affects a multitude of molecular targets including transcription factors, receptors, kinases, inflammatory cytokines, and other enzymes (for a comprehensive review see Aggarwal et al, 2007, Advances in Experimental Medicine and Biology, 595, 1-75). Curcumin modulates multiple signaling pathways including pathways involved in cell proliferation (cyclin D1, c-myc), cell survival (Bcl-2, Bcl-xL, cFLIP, XIAP, c-IAP1), and apoptosis (caspase-8, 3, 9). Other pathways affected by curcumin include those comprising protein kinases (JNK, Akt, AMPK), tumor suppressors (p53, p21), death receptors (DR4, DR5), mitochondrial pathways and endoplasmic reticulum stress responses. Curcumin has also been shown to alter the expression and function of COX2 and 5-LOX at the transcriptional and post-translational levels. Thus, it is possible, that many of the cellular and molecular effects observed in curcumin treated cells might be due to downstream effects rather than direct interactions with curcumin.

Although there are now a multitude of studies on curcumin's cellular effects, surprisingly little is known about the direct interactions of curcumin with its target molecules. One of the better characterized interactions is the binding of curcumin to the cystic fibrosis transmembrane conductance regulator (CFTR) (Bernard et al., 2009, The Journal of Biological Chemistry, 284: 30754-30765). Curcumin can crosslink CFTR polypeptides into SDS-resistant oligomers in microsomes and in intact cells. However, the ability of curcumin to rapidly and persistently stimulate CFTR channels was unrelated to the crosslinking activity.

After leukemias, brain cancers are the second most common cancers in children. In general, the prognosis for patients diagnosed with brain tumors is worse than for many other pediatric cancers and as a group account for more than a quarter of childhood deaths from cancer. Medulloblastoma, the most common brain cancer in children, is incurable in about a third of patients and survivors suffer from serious therapy-related side effects. These include cognitive and intellectual deficits in IQ, memory, attention, language and mathematical ability, hearing loss, impaired growth and bone development, endocrinological problems, and the development of secondary cancers.

Safe and effective treatment options for medulloblastoma and other cancers, and the ability to predict the response to such a treatment, is critical to patient management.

Cdc27/APC3

Spindle Assembly Checkpoint (SAC) is required to block sister chromatid separation until all chromosomes are properly attached to the mitotic apparatus. The SAC prevents cells entering anaphase by inhibiting the ubiquitination of cyclin B1 and securin by the Anaphase Promoting Complex/Cyclosome (APC/C) ubiquitin ligase. The target of the SAC is the essential APC/C activator, Cdc20.

APC/C is partially activated through phosphorylation of core subunits. One core subunit, the protein Cdc27 (also known as APC3) undergoes mitosis-specific phosphorylation which seems to enhance the affinity between APC/C and p55Cdc20, thereby ensuring its activation (King et al., 1995, Cell, 81: 279-288; Kraft et al., 2003, EMBO Journal, 22 2/1: 6598-6609; Yu et al., 2007, Molecular Cell, 27: 3-16; Kimata et al., 2008, Molecular Cell 32: 576-583). Analysis of mitosis-specific phosphorylation sites in Cdc27 has revealed that most of them are clustered in confined regions, mainly outside of the tetratrico-peptide repeats (TPR) (Kraft et al., 2003, EMBO Journal, 24: 6598-6609).

Human Cdc27 was described by Tugendreich et al., 1993, Proc. Natl. Acad Sci USA 90: 10031-10035). The amino acid sequence of Cdc27 is provided under GenBank Accession No. NP_001107563.1. The nucleotide sequence of the encoding m RNA is provided under GenBank Accession No. NM_001114091.1. Both sequences are incorporated herein by reference.

SUMMARY OF THE INVENTION

Provided is a method of identifying a patient with cancer who is most likely to benefit from treatment with an agent that binds phosphorylated Cdc27. The method comprises: (a) obtaining a sample of cancer cells from the patient; (b) determining whether the sample comprises cancer cells that contain phosphorylated Cdc27; and (c) identifying the patient as one most likely to benefit from treatment with an agent that binds phosphorylated Cdc27, if the cancer cells comprise phosphorylated Cdc27.

In embodiments, an agent that binds phosphorylated Cdc27 also crosslinks phosphorylated Cdc27, and the method is for identifying a patient with cancer who is most likely to benefit from treatment with an agent that crosslinks phosphorylated Cdc27. The method thus comprises: (a) obtaining a sample of cancer cells from the patient; (b) determining whether the sample comprises cancer cells that contain phosphorylated Cdc27; and (c) identifying the patient as one most likely to benefit from treatment with an agent that crosslinks phosphorylated Cdc27, if the cancer-cells comprise phosphorylated Cdc27.

Provided is a method of predicting whether a cancer patient is afflicted with a tumor that will respond effectively to treatment with an agent that binds phosphorylated Cdc27. The method comprises: (a) obtaining a sample of the patient's tumor; (b) determining whether the sample comprises tumor cells that contain phosphorylated Cdc27; and (c) predicting that the tumor will respond effectively to treatment with an agent that binds phosphorylated Cdc27, if tumor cells of the sample contain phosphorylated Cdc27.

In embodiments, an agent that binds phosphorylated Cdc27 also crosslinks phosphorylated Cdc27, and the method is for predicting whether a cancer patient is afflicted with a tumor that will respond effectively to treatment with an agent that crosslinks phosphorylated Cdc27. The method comprises: (a) obtaining a sample of the patient's tumor; (b) determining whether the sample comprises tumor cells that contain phosphorylated Cdc27; and (c) predicting that the tumor will respond effectively to treatment with an agent that crosslinks phosphorylated Cdc27, if tumor cells of the sample contain phosphorylated Cdc27.

Provided is a method of assessing whether a cancer patient afflicted with a tumor who is undergoing treatment with an agent that binds phosphorylated Cdc27 will continue to respond effectively to said treatment. The method comprises: (a) obtaining a sample of the patient's tumor; (b) determining whether the sample comprises tumor cells that contain phosphorylated Cdc27; and predicting that the tumor will continue to respond effectively to treatment with said agent that binds phosphorylated Cdc27, if tumor cells of the sample contain phosphorylated Cdc27.

In embodiments, the agent that binds phosphorylated Cdc27 also crosslinks phosphorylated Cdc27, and the method is for assessing whether a cancer patient afflicted with a tumor who is undergoing treatment with an agent that crosslinks phosphorylated Cdc27 will continue to respond effectively to said treatment. The method comprises: (a) obtaining a sample of the patient's tumor; (b) determining whether the sample comprises tumor cells that contain phosphorylated Cdc27; and predicting that the tumor will continue to respond effectively to treatment with said agent that crosslinks phosphorylated Cdc27, if tumor cells of the sample contain phosphorylated Cdc27.

In some embodiments of the aforesaid methods, the agent that binds phosphorylated Cdc27 preferentially binds phosphorylated Cdc27.

In some embodiments of the aforesaid methods, the agent comprises curcumin.

Provided is a method of identifying a patient with cancer who is most likely to benefit from treatment with curcumin. The method comprises: (a) obtaining a sample of cancer cells from the patient; (b) determining whether the sample comprises cancer cells that contain phosphorylated Cdc27; and (c) identifying the patient as one most likely to benefit from treatment with curcumin, if the cancer cells comprise phosphorylated Cdc27.

Provided is a method of predicting whether a cancer patient is afflicted with a tumor that will respond effectively to treatment with curcumin. The method comprises: (a) obtaining a sample of the patient's tumor; (b) determining whether the sample comprises tumor cells that contain phosphorylated Cdc27; and (c) predicting that the tumor will respond effectively to treatment with curcumin, if tumor cells of the sample contain phosphorylated Cdc27.

In some embodiments of the aforementioned methods, determining whether the sample comprises cells that contain phosphorylated Cdc27 comprises an assay that utilizes a binding agent that is specific for phosphorylated Cdc27. The binding agent may comprise, for example, an antibody or an aptamer.

In some embodiments of the aforementioned methods, the patient is afflicted with leukemia, lymphoma, multiple myeloma, gastrointestinal cancer; bladder cancer; kidney cancer; prostate cancer; breast cancer; cervical cancer; ovarian cancer; lung cancer; melanoma; brain cancer; or a combination thereof. In some embodiments, the patient is afflicted with medulloblastoma.

Also provided is a method of treating cancer in a patient, comprising: (a) determining the patient's likely responsiveness to an agent that binds phosphorylated Cdc27 by: (i) obtaining a sample of cancer cells from the patient; (ii) determining whether the cancer cells contain phosphorylated Cdc27; and (iii) identifying the patient as one most likely to benefit from treatment with an agent that binds phosphorylated Cdc27, if the cancer cells comprise phosphorylated Cdc27; and (b) administering to said patient a therapeutically effective amount of an agent that binds phosphorylated Cdc27, if the patient is determined to be likely responsive to said therapeutic agent.

In another embodiment, a method of treating cancer in a patient is provided, comprising: (a) determining the patient's likely responsiveness to an agent that crosslinks phosphorylated Cdc27 by: (i) obtaining a sample of cancer cells from the patient; (ii) determining whether the cancer cells contain phosphorylated Cdc27; and (iii) identifying the patient as one most likely to benefit from treatment with an agent that crosslinks phosphorylated Cdc27, if the cancer cells comprise phosphorylated Cdc27; and (b) administering to said patient a therapeutically effective amount of an agent that crosslinks phosphorylated Cdc27, if the patient is determined to be likely responsive to said therapeutic agent.

In some embodiments of the aforesaid treatment methods, the agent that binds phosphorylated Cdc27 preferentially binds phosphorylated Cdc27.

In some embodiments of the aforesaid treatment methods, the patient is afflicted with leukemia, lymphoma, multiple myeloma, gastrointestinal cancer; bladder cancer; kidney cancer; prostate cancer; breast cancer; cervical cancer; ovarian cancer; lung cancer; melanoma; brain cancer; or a combination thereof. In some embodiments, the patient is afflicted with medulloblastoma. In some embodiments, the administered agent comprises curcumin or an analogue, derivative or prodrug thereof.

Also provided is a method of identifying a candidate compound as being useful for modulating apoptosis of a cancer cell, the method comprising: (a) contacting a sample comprising phosphorylated Cdc27 with, a test compound under conditions that allow the test compound to bind phosphorylated Cdc27; (b) evaluating binding of said phosphorylated Cdc27 in said sample by said test compound; and (c) identifying the test compound as a candidate compound if the test compound binds phosphorylated Cdc27.

In embodiments of the method of identifying a candidate compound as being useful for modulating apoptosis of a cancer cell, an agent that binds phosphorylated Cdc27 also crosslinks phosphorylated Cdc27, and the method comprises: (a) contacting a sample comprising phosphorylated Cdc27 with a test compound under conditions that allow the test compound to crosslink phosphorylated Cdc27; (b) evaluating crosslinking of said phosphorylated Cdc27 in said sample by said test compound; and (c) identifying the test compound as a candidate compound if the test compound crosslinks phosphorylated Cdc27.

Also provided is a method of identifying a candidate compound as being useful for treating cancer, the method comprising: (a) contacting a sample comprising phosphorylated Cdc27 with a test compound under conditions that allow the test compound to bind phosphorylated Cdc27; (b) evaluating binding of said phosphorylated Cdc27 in said sample by said test compound; and (c) identifying the test compound as a candidate compound if the test compound binds phosphorylated Cdc27.

In embodiments of the method of identifying a candidate compound as being useful for treating cancer, an agent that binds phosphorylated Cdc27 also crosslinks phosphorylated, and the method comprises: a) contacting a sample comprising phosphorylated Cdc27 with a test compound under conditions that allow the test compound to crosslink phosphorylated Cdc27; (b) evaluating crosslinking of said phosphorylated Cdc27 in said sample by said test compound; and (c) identifying the test compound as a candidate compound if the test compound crosslinks phosphorylated Cdc27.

In some embodiments of the aforesaid methods for identifying a candidate compound, the agent that binds phosphorylated Cdc27 preferentially binds phosphorylated Cdc27.

In some embodiments of the aforesaid identification methods, the sample comprising phosphorylated Cdc27 comprises a cell lysate or fraction thereof containing Cdc27. In some embodiments of the aforesaid identification methods, the test compound is a biological compound, in some embodiments of the aforesaid identification methods, the test compound is a small molecule.

BRIEF DESCRIPTION OF THE DRAWINGS

FIG. 1A: DAOY cells were arrested in G1/S and the block was released in the presence of 0, 10 or 20 µM curcumin. At the indicated time points cell cycle progression was analyzed by flow cytometry. FIG. 1B: Mitotically arrested DAOY cells were released from their block in the presence of 0, 10 or 20 µM curcumin. Cell cycle profiles were determined at the indicated time points. FIG. 1C: Unsynchronized cells were treated with indicated concentrations of curcumin for 12 hours. In these experiments, G1/S-arrested DAOY cells were released from their block for 12 hours in the presence of curcumin. To obtain G2/M arrested cells utilized in these experiments, DAOY cells were synchronized first at G1/S. The block was released for 8 hours in the absence of any drugs. Cells were then treated with the indicated concentration of curcumin for an additional 12 hours. The cell-cycle dependent cytotoxicity of curcumin was measured by an LDH assay. The data of FIGS. 1A-1C represent the mean±SEM of three independent experiments.

FIG. 2A shows the expression of the APC/C subunit APC2, the APC/C co-activator p55Cdc20 and cyclins A and E in control and curcumin-treated DAOY cells as determined by immunoblotting. GAPDH levels are included to ensure equal loading. FIG. 2B is an immunoblot of the APC/C subunit Cdc27 showing a curcumin-induced shift in molecular weight (arrows). Because of differences in band intensity the same immunoblot is shown with two different exposures. Arrowhead and asterisk indicate the unphosphorylated and phosphorylated bands of Cdc27, respectively. FIG. 2C is a comparison of MW shift by curcumin between Cdc27 and other APC components. Tubulin was used for equal loading control.

In FIG. 3A, DAOY cell lysates were incubated with curcumin-bound Sepharose beads and then subjected to SDS-PAGE and immunoblotting with Cdc27. A BubR1 immunoblot was included as control for non-specific binding. In FIG. 3B, DAOY cells were incubated with either curcumin or half-curcumin for indicated time points. Cell lysates were separated by SDS-PAGE and immunoblotted for Cdc27. The middle panel in FIG. 3B shows a longer exposure of the same blot in the upper panel. FIG. 3C is a graph of LDH release as a measure of cytotoxicity of curcumin and half-curcumin in DAOY cells treated for 16 hours. Data represent mean±SEM of three independent experiments.

FIG. 5A is an immunoblot of Cdc27 in various cell lines: DAOY, NT2, D283 Med and D343 Med (brain); HCT116 (colon); HT1376 and RT4 (bladder); MDCK (kidney). The arrow indicates the band corresponding to phosphorylated Cdc27 and the arrowhead shows unphosphorylated Cdc27. Actin immunoblot is shown as a loading control. FIG. 5B is a Cdc27 immunoblot of cell lines in FIG. 5A after treatment with 20 μM curcumin for the indicated times. Arrows indicate crosslinked Cdc27, while arrowheads show phosphorylated Cdc27. Equal amounts of protein were used as shown by actin immunoblot. FIG. 5C is a graph of a cytotoxicity of curcumin in six different cell lines (DAOY, NT2. HCT116, RT4, MDCK and HT1376) with different Cdc27 phosphorylation levels. LDH release was determined after 24 hours of exposure to curcumin at indicated concentrations. Data are the mean±SEM of three independent experiments. FIG. 5D are immunoblots of cleaved PARP and caspase-3 as indicators of apoptosis upon exposure to 20 μM curcumin. Tubulin immunoblot ensures equal amounts of protein being used for analysis. Arrows indicate cleaved PARP.

In FIG. 8A, DAOY cells were released from thymidine/nocodazole block in the presence of 0, 20 and 40 μM curcumin for the indicated time points. Cell lysates were subjected to immunoblotting with the antibodies shown. The arrow indicates phosphorylated Cdc27, while the arrowhead shows unphosphorylated Cdc27. In FIG. 8B, mitotically arrested DAOY cells were released with different concentrations of curcumin for 2 and 4 hours, respectively, and blotted with the antibodies indicated. In FIG. 8C, DAOY cells were synchronized by double thymidine arrest and then incubated with curcumin for 8 hours. Cell lysates were subjected to immunoprecipitation with anti-Cdc27 antibodies. Immunoprecipitated proteins were immunoblotted with antibodies indicated. Immunoblots of total cell lysates are shown to ensure equal loading. In FIG. 8D, mitotically arrested DAOY cells were released in the presence of either DMSO or curcumin for indicated time points and APC/C activity was determined.

DEFINITIONS

Figure 1A:
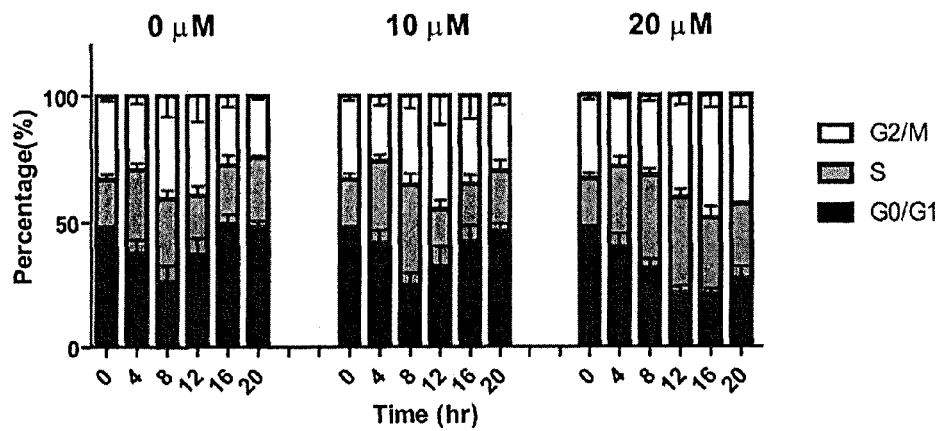
FIGS. 1A, 1B and 1C show the effect of curcumin induced cell cycle arrest in DAOY medulloblastoma cells. Curcumin preferentially induced cell cycle arrest and cell death in dividing medulloblastoma cells.

As used herein, each of the following terms has the meaning associated with it in this section.

The articles "a" and "an" are used herein to refer to one or to more than one (i.e. to at least one) of the grammatical object of the article. By way of example, "an element" means one element or more than one element.

The term "about" will be understood by persons of ordinary skill in the art and will vary to some extent depending on the context in which it is used. As used herein, "about" is meant to encompass variations of ±20% or ±10%, more preferably ±5%, even more preferably ±1%, and still more preferably ±0.1%.

The term "antibody," as used herein, refers to an immunoglobulin molecule which is able to specifically bind to a specific epitope on an antigen. Antibodies can be intact immunoglobulins derived from natural sources or from recombinant sources and can be immunoreactive portions of intact immunoglobulins. Antibodies are typically tetramers of immunoglobulin molecules. The antibodies that may be used in the practice of the present invention may exist in a variety of forms including, for example, polyclonal antibodies, monoclonal antibodies, Fv, Fab and F(ab)2, as well as single chain antibodies and humanized antibodies (Harlow et al., 1999, Using Antibodies: A Laboratory Manual, Cold Spring Harbor Laboratory Press, New York; Harlow et al., 1989, Antibodies: A Laboratory Manual, Cold Spring Harbor, N.Y.; Houston et al., 1988, Proc. Natl. Acad. Sci. USA 85:5879-5883; Bird et al., 1988, Science 242:423-426). The term "antibody" is intended to include antibody fragments that retain antigen-binding activity.

The term "cancer" in an animal refers to the presence of cells possessing characteristics typical of cancer-causing cells, such as uncontrolled proliferation, immortality, metastatic potential, rapid growth and proliferation rate, and certain characteristic-morphological features. Often, cancer cells will be in the form of a tumor, but such cells may exist alone within an animal or may circulate in the blood stream as independent cells, such as leukemic, cells.

The term "phosphorylated Cdc27" means Cdc27 which is phosphorylated at one or more serine, threonine or tyrosine residues.

The term "crosslinked phosphorylated Cdc27" means a phosphorylated Cdc27 that is dimerized or oligomerized by the action of an agent that forms crosslinks between monomeric phosphorylated Cdc27.

As used herein, an "instructional material" includes a publication, a recording, a diagram, or any other medium of expression, which can be used to communicate the usefulness of the invention in the kit for determining the progression of a disease. The instructional material of the kit of the invention may, for example, be affixed to a container, which contains a reagent of the invention or be shipped together with a container, which contains a reagent. Alternatively, the instructional material may be shipped separately from the container with the intention that the instructional material and the reagent be used cooperatively by the recipient.

"Measuring" or "measurement," or alternatively "detecting" or "detection," or alternatively "determining" or "determine", or alternatively "evaluate" or "evaluating", means assessing the presence, absence, quantity or amount of either a given substance within a sample, including the derivation of qualitative or quantitative concentration levels of such substances.

An "oligonucleotide" or "polynucleotide" is a nucleic acid ranging from at least 2, preferably at least 8, 15 or 25 nucleotides in length, but may be up to 50, 100, 1000, or 5000 nucleotides long or a compound that specifically hybridizes to a polynucleotide. Polynucleotides include sequences of deoxyribonucleic acid (DNA) or ribonucleic acid (RNA) or mimetics thereof which may be isolated from natural sources, recombinantly produced or artificially synthesized. A further example of a polynucleotide may be a peptide nucleic acid (PNA). (See U.S. Pat. No. 6,156,501.)

"Preferentially binds" as used herein in the context of the binding of a molecule to phosphorylated Cdc27 refers to a preference of the molecule to bind to phosphorylated Cdc27 over unphosphorylated Cdc27.

"Sample" or "biological sample" as used herein means a biological material that contains a substance under assay. The sample may contain any biological material suitable for detecting a desired biomarker, and may comprise cellular and/or non-cellular material.

"Specifically binds" as used herein in the context of an antibody or an aptamer refers to antibody or aptamer binding to a predetermined antigen with a preference that enables the antibody or aptamer to be used to distinguish the antigen from others to an extent that permits the detection of the target antigen described herein.

The term "treating" as used herein, unless otherwise indicated, means reversing, alleviating, inhibiting the progress of, or preventing, either partially or completely, the growth of tumors, tumor metastases, or other cancer-causing or neoplastic cells in a patient with cancer. The term "treatment" as used herein, unless otherwise indicated, refers to the act of treating. The term "treating" does not necessarily mean that cancer cells or other disorder will, in fact, be eliminated, that the number of cells will, in fact, be reduced, or that the symptoms of a cancer or other disorder will, in fact, be alleviated. Often, a method of treating cancer will be performed even with a low likelihood of success, but which, given the medical history and estimated survival expectancy of an animal, is nevertheless deemed an overall beneficial course of action.

The term "therapeutically effective amount" or "effective amount" means the amount of a subject compound or combination that will elicit the biological or medical response of a tissue, system, animal or human that is being sought.

As envisioned in the present invention with respect to the disclosed compositions of matter and methods, in one aspect the embodiments of the invention comprise the components and/or steps disclosed therein. In another aspect, the embodiments of the invention consist essentially of the components and/or steps disclosed therein. In yet another aspect, the embodiments of the invention consist of the components and/or steps disclosed therein.

DETAILED DESCRIPTION OF THE INVENTION

The present invention provides a means to predict which cancers might respond to treatment with an agent that binds to phosphorylated Cdc27. In some embodiments, the agent binds to and crosslinks phosphorylated Cdc27, and the invention provides a method to predict which cancers might respond to treatment with an agent that crosslinks phosphorylated Cdc27. In some embodiments, the invention provides a means to predict which cancers might respond to treatment with curcumin, or an analogue or derivative thereof.

It has been found that curcumin preferentially binds to a phosphorylated form of the anaphase promoting complex protein Cdc27 that is usually associated with highly proliferating cells and is part of the mitotic spindle assembly checkpoint. It has been found that curcumin crosslinks the phosphorylated protein to induce cell cycle arrest and ultimately cell death. Cancer cells in which the phosphorylated form is present are considerably more sensitive to curcumin-induced apoptosis than cancer cells or normal cells that do not express phosphorylated Cdc27. Detection of phosphorylated Cdc27 in medulloblastoma and other cancers provides a useful prognostic means to predict the effectiveness of agents that exert anticancer effect by binding to phosphorylated Cdc27, or crosslinking phosphorylated Cdc27. In particular, detection of phosphorylated Cdc27 in medulloblastoma and other cancers in which curcumin exhibits anti-tumor activity provides a useful prognostic means to predict the effectiveness of curcumin-based therapy and to monitor therapy.

Identification of Cdc27 as a target molecule that is bound by and crosslinked by the anti-cancer agent curcumin provides a means to select candidate chemotherapeutic agents, including but not limited to curcumin derivatives, analogues, metabolites and prodrugs, that are effective in binding to phosphorylated Cdc27 and may therefore serve as anticancer agents. Selection of agents that are more effective in binding phosphorylated Cdc27 than curcumin could result in more potent anti-cancer therapeutic. Phosphorylated Cdc27 provides a target for drug screening and therapeutic intervention.

As hereinafter described, evidence is provided for the first time that curcumin may directly target the SAC to inhibit progression through mitosis. As hereinafter described, curcumin binds to and crosslinks Cdc27, a component of the APC/C and critical for its function. As hereinafter described, curcumin inhibits APC/C activity, thereby preventing the degradation of cyclin B1 and securin, consequently inducing G2/M arrest. It is further shown that curcumin appears to have a greater affinity for phosphorylated Cdc27, which is usually found in mitotically active cells. As hereinafter described, cell lines that had little or no phosphorylated Cdc27 were less sensitive to curcumin-induced apoptosis. These results provide an explanation why cancer cells are more sensitive than normal cells to curcumin-induced cell death, and demonstrate for the first time that phosphorylated Cdc27 is a biomarker for effective anticancer chemotherapy, particularly curcumin-based therapy.

As hereinafter described, it has been found that curcumin can bind to Cdc27 in vitro and can crosslink Cdc27 in a variety of cell lines. While CFTR channel activation was unrelated to the cross-linking of CFTR (See Background of the Invention, supra), evidence is provided herein that crosslinking of Cdc27 by curcumin appears to affect Cdc27 functions itself.

While curcumin was able to bind to both unphosphorylated and phosphorylated Cdc27, it was observed that cells expressing phosphorylated Cdc27 were more susceptible to curcumin-induced cell death. Without wishing to be bound by any theory, it is possible that phosphorylation induces conformational changes that are more permissive for curcumin binding and/or crosslinking of the protein, and thus curcumin is more effective in these cells.

Cdc27 is one of the five APC subunits with tetratricopeptide repeats (TPR). Nevertheless, in the experiments described below, crosslinking of other APC subunits with the TPR motif was not found, suggesting that curcumin crosslinking is specific to Cdc27.

Cdc27 is considered as a core component of the APC/C that secures the interaction with substrate/coactivator complexes (Matyskiela and Morgan, 2009, *Molecular Cell*, 34: 68-80). It directly binds activator subunits such as p55Cdc20 or cdh1 and associates with mitotic checkpoint proteins including Mad2 and BubR1 (Thornton et al., 2006, *Genes & Development*, 20: 449-460). Consistent with the finding made herein that curcumin-mediated crosslinking of Cdc27 impairs its function, a delay was observed in the mitotic exit in curcumin-treated cells when compared to control cells.

Figure 8A:
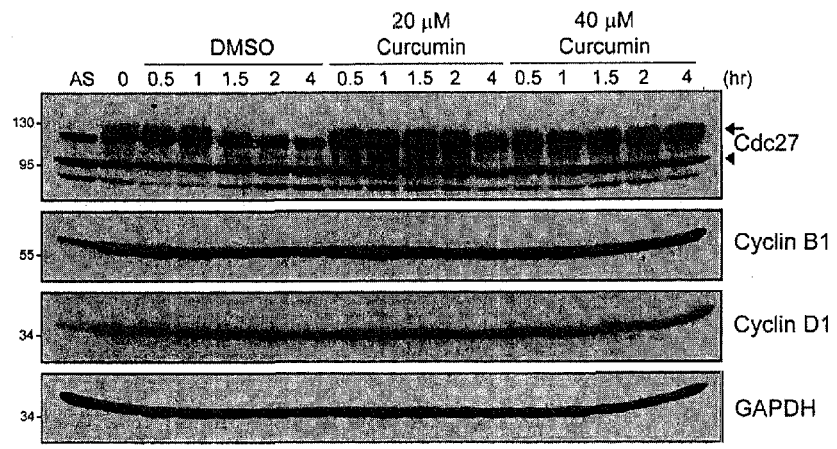
FIGS. 8A through 8D are a series of immunoblots demonstrating curcumin inhibition of APC/C activity.
Figure 8B:
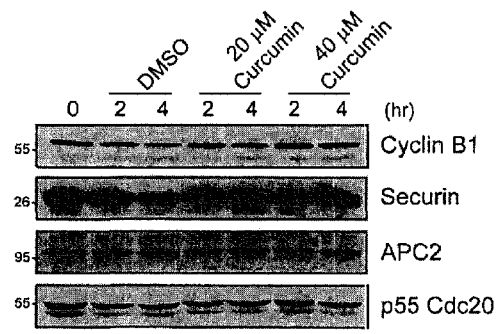
Figure 8C:
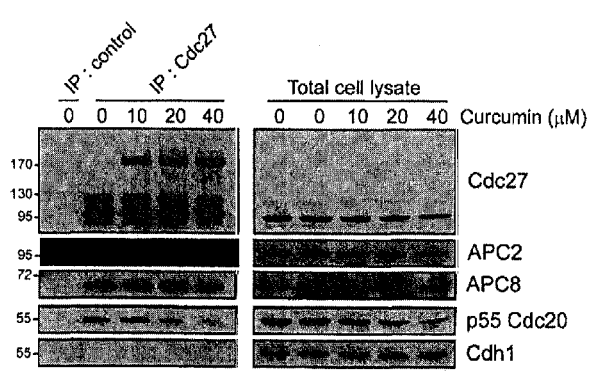

It is thought mat the SAC acts by inhibiting the p55Cdc20-bound form of the APC/C and that repression of APC/C stabilizes its downstream targets including cyclin B and securin (Nasmyth, 2002, *Science*, 297: 559-565; Peters, 2006, *Nature Reviews Molecular Cell Biology*, 7: 644-656). As hereinafter described, curcumin treatment not only blocked cyclin B1 and securin degradation but also provided a decreased association of p55Cdc20 with Cdc27 under these conditions. At the same time, association of Cdc27 with other subunits of the APC/C such as APC2 and APC8 did not change (FIG. 8C). It was found that curcumin specifically crosslinks Cdc27 and not other APC/C subunits with TPR motifs. Thus, without wishing to be bound by any theory, curcumin may repress APC/C function by preventing the efficient association of the APC/C core complex with its activator p55Cdc20. Without wishing to be bound by any theory, it is possible that curcumin blocks the phosphorylated interaction sites directly or induces a conformational change in Cdc27 that is less permissive to p55Cdc20 binding. It is also conceivable that curcumin binding to Cdc27 itself presents a steric hindrance for p55Cdc20 to access its binding sites.

Figure 9:
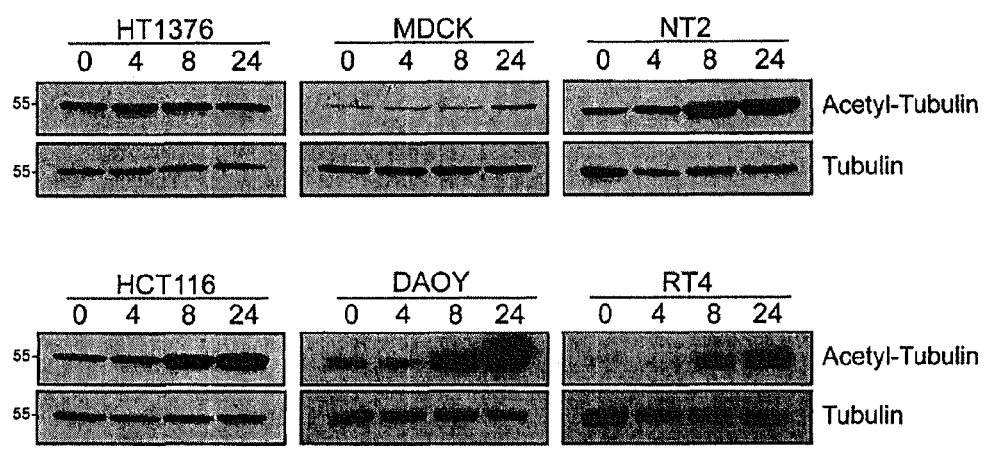
FIG. 9 is a blot showing curcumin-induced acetylated tubulin accumulation in cell lines HT1376, MDCK, NT2, HCT116; DAOY and RT4 incubated with 20 μM curcumin for 0, 4, 8 and 24 hours.

It was found that in cells with low levels of phosphorylated Cdc27 (cells in which curcumin failed to cross-link Cdc27 and which were less sensitive to curcumin treatment), curcumin-induced tubulin acetylation was also reduced (FIG. 9). Thus, loss of Cdc27 function or p55Cdc20 association with Cdc27 might be linked to increased tubulin acetylation in curcumin-treated cells.

In one embodiment, the invention provides a method of identifying a candidate compound as being useful for modulating apoptosis of a cancer cell and/or as being useful for treating cancer. The method comprises: (a) contacting a sample comprising phosphorylated Cdc27 with a test compound under conditions that allow the test compound to bind to (or to bind to and crosslink) phosphorylated Cdc27; (b) evaluating binding (or crosslinking) of the phosphorylated Cdc27 in said sample by said test compound; and (c) identifying the test compound as a candidate compound if the test compound binds (or crosslinks) phosphorylated Cdc27.

The sample comprising phosphorylated Cdc27 may comprise purified phosphorylated Cdc27, or may comprise a cell lysate or other cell fraction known to contain phosphorylated Cdc27 in a form that is available for binding, and preferably crosslinking, upon contact with a candidate compound. The sample may comprise phosphorylated Cdc27 in isolation, or may comprise phosphorylated Cdc27 complexed with one or more other members of the anaphase-promoting complex (APC). In some embodiments, the sample may comprise a cell lysate of a cell known to contain phosphorylated Cdc27, such as the cell lines DAOY and HCT116, which contain relatively high levels of phosphorylated Cdc27; the cell lines RT4 and NT2, which contain intermediate levels of phosphorylated Cdc2-7; and cell lines HT1376 and MDCK, which contain relatively low levels of phosphorylated Cdc27. Representative conditions for preparation of cell lysates are described in the Materials and Methods, infra.

Biological sources, e.g., cell lysates, may be screened for phosphorylated Cdc27 content by any of method for identifying the presence of phosphorylated Cdc27. In one embodiment, the presence of phosphorylated Cdc27 is detected by means of an antibody binding assay utilizing an antibody that is specific for a phosphorylated form of Cdc27 and does not cross-react appreciably with unphosphorylated Cdc27. Alternatively, antibody that is not specific to phosphorylated CDc27 may be utilized to detect the phosphorylated form, with a molecular weight discrimination assay that distinguishes phosphorylated Cdc27 from non-phosphorylated CDC27 on the basis of molecular weight. One such antibody-based method that combines antigen detection by antibody binding and antigen molecular weight discrimination comprises a conventional immunoblot assay. See, for example, Example 5 and FIGS. 5A, 5B and 5C infra which show discrimination of phosphorylated CDc27 (arrow in the figures) from unphosphorylated Cdc27 (arrowhead in the figures) in an immunoblot using anti-Cdc27 antibody.

The test compound is contacted with the sample comprising phosphorylated Cdc27 under conditions that allow the test compound to bind to phosphorylated Cdc27, such as in physiological buffers, cell culture media or in in vivo conditions. The mixture is then evaluated for binding of the test sample to phosphorylated Cdc27 in the sample. Suitable assay method for determining the binding of the test compound to phosphorylated Cdc27 include, for example, fluorogenic binding assays, fluid phase binding assays, affinity chromatography, size exclusion or gel filtration, ELISA, immunoprecipitation, competitive binding assays, gel shift assays, and mass spectrometry based methods.

The test compound may be further evaluated to determine that it preferentially binds phosphorylated Cdc27. Accordingly, the test compound may be contacted with a sample comprising unphosphorylated Cdc27, and the mixture is then evaluated for binding of the test sample to the unphosphorylated Cdc27 by methods described above.

Figure 2A:
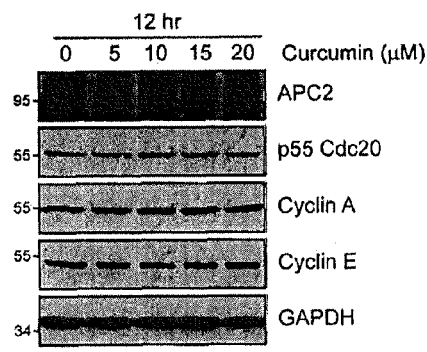
FIGS. 2A, 2B and 2C demonstrate curcumin-induced effects on APC/C and other cell cycle related proteins. Curcumin induces a molecular weight shift in Cdc27 but not in other cell-cycle related proteins often affected in cell cycle arrest.
Figure 2B:
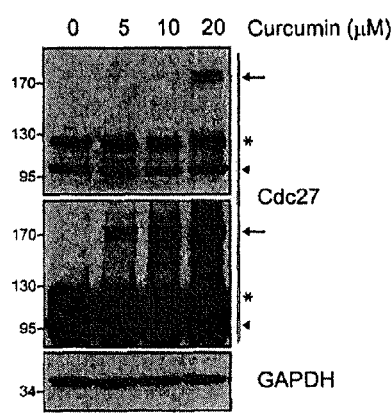

In another embodiment, the mixture is evaluated for crosslinking of the phosphorylated Cdc27 in the sample by action of the test compound. Crosslinking of the phosphorylated Cdc27 may be observed, for example, by an increase in molecular weight to at least approximately double the molecular weight of uncrosslinked phosphorylated Cdc27. An example of this molecular weight shift upon crosslinking by curcumin is shown in FIG. 2B. Arrowhead and asterisk indicate the non- and phosphorylated bands of Cdc27, respectively. The curcumin-induced shift in Cdc27 molecular weight is indicated by the arrows. Because of differences in band intensity the same immunoblot is shown with two different exposures in FIG. 2B.

The candidate compound for screening in the above procedure for detection of phosphorylated Cdc27 binding and/or crosslinking activity may comprise any chemical substance that may ultimately be suitable for therapeutic administration. Such substances include, for example, biological molecules such as nucleic acids, antibodies, antigen-binding fragments thereof, polynucleotides, peptides or polypeptides, and small molecule compounds including both organic and inorganic compounds. By "small molecule" is meant an organic or inorganic compound of molecular weight of below about 3,000 Daltons. The candidate compounds may be isolated from natural sources or synthesized. Small molecule test compounds can initially be members of an organic or inorganic chemical library.

Small molecules can be natural products or members of a combinatorial chemistry library. A set of diverse molecules maybe screened to cover a variety of functions such as charge, aromaticity, hydrogen bonding, flexibility, size, length of side chain, hydrophobicity, and rigidity. Combinatorial techniques suitable for synthesizing small molecules are known in the art, e.g., as exemplified by Obrecht and Villalgordo, *Solid-Supported Combinatorial and Parallel Synthesis of Small-Molecular-Weight Compound Libraries*, Pergamon-Elsevier Science Limited (1998), and include those such as the "split and pool" or "parallel" synthesis techniques, solid-phase and solution-phase techniques, and encoding techniques (see, for example, Czarnik, *Curr. Opin. Chem. Bio.*, 1:60 (1997). In addition, a number of small molecule libraries are commercially available.

In one embodiment, the candidate compound is an analogue, derivative or prodrug of curcumin. There are several curcumin analogs that include the natural curcuminoids demethoxycurcumin and bisdemethoxycurcumin and synthesized analogs such as curcumin derivatives. By "curcumin derivative" is meant a compound that retains the basic structural features of curcumin but include modifications such as acetylation, alkylation, glycosylation, and amino acetylation of the phenolic hydroxyl group; demethylation of the methoxy groups; or acetylation, alkylation and substitution of the reactive methylene group of the linker, among others modifications. Derivatives also include metal complexes of curcumin. By "curcumin analog" is meant that has structural analogy to curcumin, and includes natural compounds such as ferulic acid, cinnamic acid, caffeic acid, capsaicin, and gingerol. By "prodrug" is meant a compound which, upon administration, cleaves to or converts to curcumin inside the body of the recipient.

In another embodiment, a method is provided for identifying a patient with cancer who is most likely to benefit from treatment with an agent that, binds to or crosslinks phosphorylated Cdc27. The method comprises (a) obtaining a sample of cancer cells from the patient, (b) determining whether the sample comprises cancer cells that contain phosphorylated Cdc27; and identifying the patient as one most likely to benefit from treatment with an agent that binds to or crosslinks phosphorylated Cdc27, if the cancer cells comprise phosphorylated Cdc27. In one embodiment, the method is for identifying the patient as one would most likely benefit from treatment with curcumin.

In another embodiment, a method is provided for predicting whether a cancer patient is afflicted with a tumor that will respond effectively to treatment with an agent that binds to or crosslinks phosphorylated Cdc27. The method comprises: (a) obtaining a sample of the patient's tumor; (b) determining whether the sample comprises tumor cells that contain phosphorylated Cdc27; and (c) predicting that the tumor will respond effectively to treatment with an agent that binds to or crosslinks phosphorylated Cdc27, if tumor cells of the sample contain phosphorylated Cdc27.

In another embodiment, a method is provided for assessing whether a cancer patient afflicted with a tumor who is undergoing treatment with an agent that binds to or crosslinks phosphorylated Cdc27 will continue to respond effectively to said treatment. The method comprises: (a) obtaining a sample of the patient's tumor; (b) determining whether the sample comprises tumor cells that contain phosphorylated Cdc27; and (c) predicting that the tumor will continue to respond effectively to treatment with said agent that binds to or crosslinks phosphorylated Cdc27, if tumor cells of the sample contain phosphorylated Cdc27.

The cancer cell or tumor sample for use in the above methods may be obtained from the patient according to conventional cell harvesting or biopsy techniques. Cancer cells may comprise cells from a tumor, or from a non-solid malignancy, such as a leukemia, or from circulating tumor cells isolated from a blood sample, e.g., a sample of peripheral blood. The cancer cells or tumor sample is processed in a manner that will make available phosphorylated Cdc27 for detection, if contained in the cells. Typically, this goal is accomplished by preparing, a cell lysate, or fraction thereof containing cellular proteins, or a fraction of cellular proteins containing APC/C, of which Cdc27 is a component. A representative cell lysis technique for creating a cell lysate for rendering Cdc27 available for detection is described in the Materials and Methods, infra.

The sample is then assayed for the presence of phosphorylated Cdc27. Any assay method which specifically identifies phosphorylated Cdc27 over unphosphorylated Cdc27 may be utilized. Such methods may utilize a substance comprising a binding agent that is specific for phosphorylated Cdc27. Assays based on protein-specific biomolecule interaction include, but are not limited to, antibody-based assays, aptamer-based assays, receptor and ligand assays, enzyme activity assays, and allosteric regulator binding assays. The invention is not limited to any one method of protein detection, but rather encompasses all presently known or heretofore unknown methods, such as methods that are discovered in the art. Proteins may be detected by other methods, e.g., mass spectroscopy analysis, that do not relying on a binding moiety.

In one embodiment, the binding moiety comprises an antibody that specifically binds to phosphorylated Cdc27. The preparation of antibodies specific for phosphorylated forms of proteins, so-called "phosphosite-specific", antibodies is well-known. Such methods are reviewed in Brumbaugh ex al. "Overview of the Generation, Validation, and Application of Phosphosite-Specific Antibodies", Chapter 1, p. 3-43, in *Signal Transduction Immunohistochemistry: Methods and Protocols*, Vol. 717, Alexander E. Kalyuzhny (ed.), Springer Science+Business Media, LLC (2011). Phosphorylation sites on Cdc27 are descried by Kraft et al., 2003. *EMBO J.*, 24:6598-6609. Antibodies can be used in various immunoassay-based protein determination methods such as Western blot analysis, immunoprecipitation, radioimmunoassay (RIA), immunofluorescent assay, chemiluminescent assay, flow cytometry, immunocytochemistry and enzyme-linked immunosorbent assay (ELISA).

In an enzyme-linked immunosorbent assay (ELISA), an enzyme such as, but not limited to, horseradish peroxidase (HRP), alkaline phosphatase (AP), beta-galactosidase or urease can be linked, for example, to an antigen antibody or to a secondary antibody for use in a method of the invention. A horseradish-peroxidase detection system may be used, for example, with the chromogenic substrate tetramethylbenzidine (TMB), which yields a soluble product in the presence of hydrogen peroxide that is detectable at 450 nm. Other convenient enzyme-linked systems include, for example, the alkaline phosphatase detection system, which may be used with the chromogenic substrate p-nitrophenyl phosphate to yield a soluble product readily detectable at 405 nm. Similarly, a beta-galactosidase detection system may be used with the chromogenic substrate o-nitrophenyl-beta-D-galactopyranoside (ONPG) to yield a soluble product detectable at 410 nm. Alternatively, a urease detection system may be used with a substrate such as urea-bromocresol purple (Sigma Immunochemicals, St. Louis, Mo.). Useful enzyme-linked primary and secondary antibodies can be obtained from any number of commercial sources.

For chemiluminescence and fluorescence assays, chemiluminescent and fluorescent secondary antibodies may be obtained from any number of commercial sources. Fluorescent detection is also useful for detecting antigen or for determining a level of antigen in a method of the invention. Useful fluorochromes include, but are not limited to, DAPI, fluorescein, Hoechst 33258, R-phycocyanin, B-phycoerythrin, R-phycoerythrin, rhodamine, Texas red and lissamine-Fluorescein- or rhodamine-labeled antigen-specific antibodies.

Radioimmunoassays (RIAs) are described for example in Brophy et al. (1990, *Biochem. Biophys. Res. Comm.* 167:898-

903) and Guechot et al. (1996, *Clin. Chem.* 42:558-563). Radioimmunoassays are performed, for example, using Iodine-125-labeled primary or secondary antibody.

Western blotting may also be used to detect and or determine the level of phosphorylated Cdc27. Western blots may be quantified using well known methods such as scanning densitometry (Parra et al., 1998, *J. Vasc. Surg.* 28:669-675).

A signal emitted from a detectable antibody is analyzed, for example, using a spectrophotometer to detect color from a chromogenic substrate; a radiation counter to detect radiation, such as a gamma counter for detection of Iodine-125; or a fluorometer to detect fluorescence in the presence of light of a certain wavelength. Where an enzyme-linked assay is used, quantitative analysis of the amount of antigen is performed using a spectrophotometer. It is understood that the assays of the invention can be performed manually or, if desired, can be automated and that the signal emitted from multiple samples can be detected simultaneously in many systems available commercially. Antigen-antibody binding can also be detected, for example, by mass spectrometry.

The antibody used to detect phosphorylated Cdc27 in a sample in an immunoassay can comprise a polyclonal or monoclonal antibody. The antibody can comprise an intact antibody, or antibody fragments capable of specifically binding antigen. Such fragments include, but are not limited to, Fab and F(ab')$_2$ fragments.

Techniques for detecting and quantifying (such as with respect to a control) antibody binding are well-known in the art. Antibody binding to phosphorylated Cdc27 may be detected through the use of chemical reagents that generate a detectable signal that corresponds to the level of antibody binding and, accordingly, to the level of marker protein expression. Examples of such detectable substances include enzymes, prosthetic groups, fluorescent materials, luminescent materials, bio luminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin; and examples of suitable radioactive material include $^{125}$I, $^{131}$I, $^{35}$S, or $^3$H.

Antibody binding may be detected through the use of a secondary antibody that is conjugated to a detectable label. Examples of detectable labels include but are not limited to polymer-enzyme conjugates. The enzymes in these complexes are typically used to catalyze the deposition of a chromogen at the antigen-antibody binding site, thereby resulting in cell staining that corresponds to expression level of the biomarker of interest. Preferred enzymes of particular interest. Include horseradish peroxidase (HRP) and alkaline phosphatase (AP).

Phosphorylated Cdc27 can be detected and quantified by aptamer-based assays, which are very similar to antibody-based assays, but with/the use of an aptamer instead of an antibody. An "aptamer-based" assay is thus an assay for the determination of polypeptide that relies on specific binding of an aptamer. An aptamer can be any polynucleotide, generally a RNA or a DNA, which has a useful biological activity in terms of biochemical activity or molecular recognition attributes. Usually, an aptamer has a molecular activity such as having an enzymatic activity or binding to a polypeptide at a specific region (i.e., similar to an epitope for an antibody) of the polypeptide. It is generally known in the art that an aptamer can be made by in vitro selection methods. In vitro selection methods include a well-known method called systematic evolution of ligands by exponential enrichment (a.k.a. SELEX). Briefly, in vitro selection involves screening a pool of random polynucleotides for a particular polynucleotide that binds to a biomolecule, such as a polypeptide, or has a particular activity that is selectable. Generally, the particular polynucleotide represents a very small fraction of the pool, therefore, a round of amplification, usually via polymerase chain reaction, is employed to increase the representation of potentially useful aptamers. Successive rounds of selection and amplification are employed to exponentially increase the abundance of a particular aptamer. In vitro selection is described in Famulok, M.; Szostak, J. W., In Vitro Selection of Specific Ligand Binding Nucleic Acids, *Angew. Chem.* 1992, 104, 1001. (*Angew. Chem. Int. Ed. Engl.* 1992, 31, 979-988.); Famulok, M.; Szostak, J. W., Selection of Functional RNA and DNA Molecules from Randomized Sequences, *Nucleic Acids and Molecular Biology*, Vol. 7, F. Eckstein, D. M. J. Lilley, Eds. Springer Verlag, Berlin, 1993, pp. 271; Klug, S.; Famulok, M., All you wanted to know about SELEX; *Mol. Biol. Reports* 1994, 20, 97-107; and Burgstaller, P.; Famulok, M. Synthetic ribozymes and the first deoxyribozyme; *Angew. Chem.* 1995, 107, 1303-1306 (*Angew. Chem. Int. Ed. Engl.* 1995, 34, 1189-1192), U.S. Pat. No. 6,287,765, U.S. Pat. No. 6,180,348, U.S. Pat. No. 6,001,570, U.S. Pat. No. 5,861,588, U.S. Pat. No. 5,567,588, U.S. Pat. No. 5,475,096, and U.S. Pat. No. 5,270,163, which are incorporated herein by reference.

Substantially pure phosphorylated Cdc27, which can be used as an immunogen for raising polyclonal or monoclonal antibodies, or as a substrate for selecting aptamers, can be prepared, for example, by recombinant DNA methods. For example, the cDNA of the marker protein can be cloned into an expression vector by techniques within the skill in the art. An expression vector comprising sequences encoding the maker protein can then be transfected into an appropriate eukaryotic host, whereupon the protein is expressed. The expressed protein can then be isolated by any suitable technique.

Phosphorylated Cdc27 can be detected by any of the well-known mass spectrometry methods that have been adapted for identification or detection of phosphorylated proteins. Such methods are reviewed in Palumbo et al., *Mass Spectrometry Reviews* 30:600-625 (2013).

Figure 6:
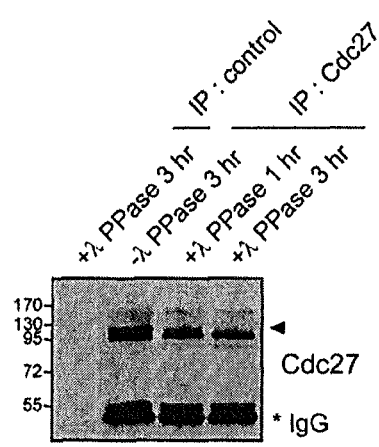
FIG. 6 is a blot of immunoprecipitated Cdc27 from DAOY cells. Immunoprecipitated Cdc27 was incubated with or without λ-phosphatase for indicated time points and then resolved in SDS-PAGE for Western blotting. The arrowhead indicates phosphorylated Cdc27 and the asterisk indicates IgG of input antibodies.

In one embodiment, detection of phosphorylated Cdc27 in the sample is carried out using an immunoblot method that relies on electrophoretic separation of proteins from a cell sample lysate and detection with specific antibody. In another embodiment, phosphorylated Cdc27 is immunoprecipitated by specific antibody. In another embodiment, phosphorylated Cdc27 is detected by immunoprecipitating Cdc27 with an antibody specific for Cdc27 but may not distinguish phosphorylated from the unphosphorylated form, and then incubating the immunoprecipitated Cdc27 with or without an agent that removes phosphate groups, e.g., λ-phosphatase. The phosphatase-treated and untreated aliquots of Cdc27 are then subject to resolution by electrophoresis and Western blotting by anti-Cdc27 antibody. Phosphorylated Cdc27 appears at a higher molecular weight in comparison to unphosphorylated and phosphatase-treated Cdc27. See Example 6, infra, and FIG. 6. In FIG. 6, the arrowhead indicates phosphorylated Cdc27 and the asterisk indicates IgG of input antibodies.

The cancer patient who is tested for responsiveness to treatment with an agent that binds to or crosslinks phosphorylated Cdc27, or for continued responsiveness in a course of ongoing treatment, may be a patient afflicted with any of a variety of cancers or tumors. The cancer or tumor may be, for example, lung cancer, non small cell lung (NSCL) cancer, bronchioloalveolar cell lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, gastric cancer, colon cancer, colorectal cancer, breast cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, cancer of the bladder, cancer of the kidney or ureter, renal cell carcinoma, carcinoma of the renal pelvis, mesothelioma, hepatocellular cancer, biliary cancer, chronic or acute leukemia, lymphocytic lymphoma, neoplasm of the central nervous system (CNS), spinal axis tumors, brain stem glioma, glioblastoma multiforme, astrocytoma, schwannoma, ependymoma, medulloblastoma, meningioma, squamous cell carcinoma, pituitary adenoma, including refractory versions of any of the above cancers, or a combination of one or more of the above cancers.

In some embodiments, the cancer patient who is tested for responsiveness to treatment with an agent that binds to or crosslinks phosphorylated Cdc27 is a patient afflicted with a cancer that has been shown or proposed to be treatable with curcumin. Such cancers include, for example, hematological cancers, i.e. leukemias and lymphomas such as acute lymphoblastic leukemia (ALL), acute T cell leukemia (ATL), acute myelogenous leukemia (AML), promyeolocytic leukemia, erythromyeloblastoid leukemia, Burkitt's lymphoma, Hodgkin's lymphoma, Non-Hodgkin's lymphoma, follicular lymphoma, and primary effusion lymphoma; multiple myeloma; gastrointestinal cancers e.g., cancers of the esophagus, intestine, liver, pancreas, colon and rectum; bladder cancer; kidney cancer; prostate cancer; breast cancer; cervical cancer; ovarian cancer; lung cancer; melanoma; and brain cancer.

The afflicted patient may be an adult or a juvenile. The latter include all non-adult individuals, i.e. infants, toddlers and adolescents. In one embodiment, the afflicted patient suffers from a medulloblastoma. In one embodiment, the medulloblastoma-afflicted individual is a juvenile.

The methods of identifying candidate compounds as being useful for modulating apoptosis of cancer cells and/or as being useful for the treating cancer can be readily adapted to kit form. The methods for identifying and monitoring patients who would benefit from or be responsive to treatment with an agent that binds to or crosslinks phosphorylated Cdc27 may also be adapted to kit form.

For the candidate compound-screening method, the kit comprises a sample comprising phosphorylated Cdc27, one or more reagents and/or diluents for facilitating contact of phosphorylated Cdc27 with a candidate compound and binding to or cross-linking of said of phosphorylated Cdc27. For the patient screening method, the kit comprises a reagent specific for detection of phosphorylated Cdc27, and one or more reagents and/or diluents for facilitating the contact of the reagent and phosphorylated Cdc27. The kit may further comprise instructions for using the kit according to one or more methods of the invention.

Each kit may comprise an antibody, an antibody derivative, or an antibody fragment specific to Cdc27 for signaling crosslinking of phosphorylated Cdc27, or an antibody, an antibody derivative, or an antibody fragment specific for phosphorylated Cdc27.

The antibody may be detectably labeled, as described above. The kit can further comprise components necessary for detecting the detectable label (e.g., an enzyme or a substrate), and instrumentation for detection and measurement.

Depending on the procedure, the kit may further comprise one or more of: extraction buffer and/or reagents, amplification buffer and/or reagents, hybridization buffer and/or reagents, immunodetection buffer and/or reagents, labeling buffer and/or reagents, and detection means. Protocols for using these buffers and reagents for performing different steps of the procedure may also be included in the kit.

Reagents may be supplied in a solid (e.g., lyophilized) or liquid form. Kits of the present invention may optionally comprise different containers (e.g., vial, ampoule, test tube, flask or bottle) for each individual buffer and/or reagent. Each component will generally be suitable as aliquoted in its respective container or provided in a concentrated form. Other containers suitable for conducting certain steps for the disclosed methods may also be provided. In certain embodiments, the kits of the present invention further comprise control samples.

The instructional material may comprise a publication, a recording, a diagram, or any other medium of expression which can be used to communicate the usefulness of the method. The package insert may comprise text housed in any physical medium, e.g., paper, cardboard, film, or may be housed in an electronic medium such as a diskette, chip, memory stick or other electronic storage form. The instructional material, of the kit of the invention may, for example, be affixed to a container which contains other contents of the kit, or be shipped together with a container which contains the kit. Alternatively, the instructional material may be shipped separately from the container with the intention mat the instructional material aid the contents of the kit be used cooperatively by the recipient.

In another embodiment, a method of treating cancer in a patient, is provided. The method comprises: (a) determining the patient's likely responsiveness to an agent that binds to or crosslinks phosphorylated Cdc27 by (i) obtaining a sample of cancer cells from the patient; (ii) determining whether the cancer cells contain phosphorylated Cdc27; and (iii) identifying the patient as one most likely to benefit from treatment with an agent that binds to or crosslinks phosphorylated Cdc27, if the cancer cells comprise phosphorylated Cdc27; and (b) administering to said patient a therapeutically effective amount of an agent that binds to or crosslinks phosphorylated Cdc27. If the patient is determined to be likely responsive to said therapeutic agent.

Methods for determination of whether an agent is capable of binding to or crosslinking phosphorylated Cdc27 are described above. In one embodiment, the agent is curcumin, or an analogue, derivative or prodrug thereof. In some embodiments, the patient is afflicted with a cancer as set forth above. In particular embodiments, the patient is afflicted with a medulloblastoma, especially a juvenile afflicted with medulloblastoma.

The active agent capable of binding to or crosslinking phosphorylated Cdc27 may be administered in the form of a pharmaceutical composition, in combination with a pharmaceutically acceptable carrier. The active ingredient in such formulations may comprise from 0.1 to 99.99 weight percent "Pharmaceutically acceptable carrier" means any carrier, diluent or excipient which is compatible with the other ingredients of the formulation and not deleterious to the recipient.

The active agent is preferably administered with a pharmaceutically acceptable carrier selected on the basis of the selected route of administration and standard pharmaceutical practice. The active agent may be formulated into dosage forms according to standard practices in the field of pharmaceutical preparations. See Alphonso Gennaro, ed., *Remington's Pharmaceutical Sciences:* 18th Edition (1990), Mack Publishing Co., Easton, Pa. Suitable dosage forms may comprise, for example, tablets, capsules, solutions, parenteral solutions, troches, suppositories, or suspensions.

For parenteral administration, the active agent may be mixed, with a suitable carrier or diluent such as water, an oil (particularly a vegetable oil), ethanol, saline solution, aqueous dextrose (glucose) and related sugar solutions, glycerol, or a glycol such as propylene glycol or polyethylene glycol. The active agent may be encapsulated in liposomes or nanoparticles to improve oral bioavailability. Nanoparticulate formulation may be prepared based on poly (lactide-co-glycolide) (PLGA) and a stabilizer polyethylene glycol (PEG)-5000, for example. See, e.g., Bisht et al., *Journal of Nanobiotechnology* 2007; 5:3, describing the preparation of nanoparticle-encapsulated curcumin. Solutions for parenteral administration preferably contain a water soluble salt of the active agent. Stabilizing agents, antioxidant agents and preservatives may also be added. Suitable antioxidant agents include sulfite, ascorbic acid, citric acid and its salts, and sodium EDTA. Suitable preservatives include benzalkonium chloride, methyl- or propylparaben, and chlorbutanol. The composition for parenteral administration may take the form of an aqueous or non-aqueous solution, dispersion, suspension or emulsion.

For oral administration, the active agent may be combined with one or more solid inactive ingredients for the preparation of tablets, capsules, pills, powders, granules or other suitable oral dosage forms. For example, the active agent may be combined with at least one excipient such as fillers, binders, humectants, disintegrating agents, solution retarders, absorption accelerators, wetting agents absorbents or lubricating agents. According to one tablet embodiment, the active agent may be combined with carboxymethylcellulose calcium, magnesium stearate, mannitol and starch, and then formed into tablets by conventional tableting methods.

The specific dose of a compound according to the invention to obtain therapeutic benefit for treatment of a cancer will, of course, be determined by the particular circumstances of the individual patient including the size, weight, age and sex of the patient, the nature and stage of the cellular proliferative disorder, the aggressiveness of disorder, and the route of administration of the compound. For example, a daily dosage from about 0.05 to about 50 mg/kg/day may be utilized, more preferably from about 0.1 to about 10 mg/kg/day. Higher or lower doses are also contemplated as it may be necessary to use dosages outside these ranges in some cases. The daily dosage may be divided, such as being divided equally into two to four times per day daily dosing. The compositions are preferably formulated in a unit dosage form, each dosage containing from about 1 to about 500 mg, more typically, about 10 to about 100 mg of active agent per unit dosage. The term "unit dosage form" refers to physically discrete units suitable as a unitary dosage for human subjects and other mammals, each unit containing a predetermined quantity of active material calculated to produce the desired therapeutic effect, in association with a suitable pharmaceutical excipient.

Pharmaceutical compositions of the present invention may also be formulated so as to provide slow or controlled release of the active ingredient therein using, for example, hydropropylmethyl cellulose in varying proportions to provide the desired release profile, other polymer matrices, gels, permeable membranes, osmotic systems, multilayer coatings, microparticles, nanoparticles, liposomes, and/or microspheres.

In general, a controlled-release preparation is a pharmaceutical composition capable of releasing the active ingredient at the required rate to maintain constant pharmacological activity for a desirable period of time. Such dosage forms provide a supply of a drug to the body during a predetermined period of time and thus maintain drug levels in the therapeutic range for longer periods of time than conventional non-controlled formulations.

U.S. Pat. No. 5,674,533 discloses controlled-release pharmaceutical compositions in liquid dosage forms for the administration of moguisteine, a potent peripheral antitussive. U.S. Pat. No. 5,059,595 describes the controlled-release of active agents by the use of a gastro-resistant tablet for the therapy of organic mental disturbances. U.S. Pat. No. 5,591,767 describes a liquid reservoir transdermal patch for the controlled administration of ketorolac, a non-steroidal anti-inflammatory agent with potent analgesic properties. U.S. Pat. No. 5,120,548 discloses a controlled-release drug delivery device comprised of swellable polymers. U.S. Pat. No. 5,073,543 describes controlled-release formulations containing a trophic factor entrapped by a ganglioside-liposome vehicle. U.S. Pat. No. 5,639,476 discloses a stable solid controlled-release formulation having a coating derived from an aqueous dispersion of a hydrophobic acrylic polymer. Biodegradable microparticles are known for use in controlled-release formulations. U.S. Pat. No. 5,354,566 discloses a controlled-release powder that contains the active ingredient. U.S. Pat. No. 5,733,566 describes the use of polymeric microparticles that release antiparasitic compositions.

The controlled-release of the active ingredient may be stimulated by various inducers, for example pH, temperature, enzymes, water, or other physiological conditions or compounds. Various mechanisms of drug release exist. For example, in one embodiment, the controlled-release component may swell and form porous openings large enough to release the active ingredient after administration to a patient. The term "controlled-release component" in the context of the present invention is defined herein as a compound or compounds, such as polymers, polymer matrices, gels, permeable membranes, liposomes and/or microspheres, that facilitate the controlled-release of the active ingredient in the pharmaceutical composition. In another embodiment, the controlled-release component is biodegradable, induced by exposure to the aqueous environment, pH, temperature, or enzymes in the body. In another embodiment, sol-gels may be used, wherein the active ingredient is incorporated into a sol-gel matrix that is a solid at room temperature. This matrix is implanted into a patient, preferably a mammal, having a body temperature high enough to induce gel formation of the sol-gel matrix, thereby releasing the active ingredient into the patient.

The active agent may be administered by any route, including oral, rectal, sublingual, and parenteral administration. Parenteral administration includes, for example, intravenous, intramuscular, intraarterial, intraperitoneal, intrathecal, intracerebral intracerebroventricular, intranasal, intravaginal, intravesical (e.g., to the bladder), intradermal, transdermal, topical or subcutaneous administration. Also contemplated is the instillation of a drug in the body of the patient in a controlled formulation, with systemic or local release of the drug to occur at a later time. For example, the drug may be localized in a depot for controlled release to the circulation, or for release to a local site of tumor growth.

One or more active agents useful in the practice of the present invention may be administered simultaneously, by the same or different routes, or at different times during treatment. The compounds may be administered before, along with, or after other medications, including other antiproliferative compounds.

The treatment may be carried out for as long a period as necessary, either in a single, uninterrupted session, or in discrete sessions. The treating physician will know how to increase, decrease, or interrupt treatment based on patient response. According to one embodiment, treatment is carried out for from about four to about sixteen weeks. The treatment schedule may be repeated as required. As indicated above, the patient may be monitored for continued responsiveness to drag by monitoring the continued appearance of phosphorylated Cdc27 in the neoplastic lesion.

In some embodiments, methods described herein include the step of determining the binding of an agent to phosphorylated Cdc27. Agents that are so identified may then be further screened to identify those agents that inhibit a function of Cdc27. One such function of Cdc27 is to cause the efficient associate of the APC/C core complex with its activator p55Cdc20. Agents may be assayed for ability to reduce Cdc27 associate with p55Cdc20, and thereby to inhibit APC activity.

The practice of the invention is illustrated by the following non-limiting example. The invention should not be construed to be limited solely to the compositions and methods described herein, but should be construed to include other compositions and methods as well. One of skill in the art will know that other compositions and methods are available to perform the procedures described herein.

Materials and Methods

The following materials and methods were utilized in the Examples that follow.

A. Cell Lines and Reagents

All cell lines were obtained from the American Type Culture Collection (ATCC, Manassas, Va.) and cultured according to ATCC protocols. The human medulloblastoma cell line DAOY was cultured in MEM supplemented with 10% fetal bovine serum, glutamine and penicillin/streptomycin in a humidified, 5% $CO_2$ atmosphere at 37°.

Antibodies against α-tubulin, acetylated α-tubulin, cleaved caspase-3, cleaved PARP, GAPDH, cyclin A, and cyclin D1 and horseradish peroxidase (HRP)-conjugated secondary antibodies were obtained from Cell Signaling Technology (Danvers, Mass.), APC2, APC7, and APC8 from Biolegend (San Diego, Calif.) and Cdc27, Cdc20, BubRI, and β-actin from BD Transduction Laboratories (Franklin Lakes, N.J.). Antibody against cyclin B1 was purchased from Santa. Cruz Biotechnology (Santa Cruz, Calif.) and securin from Abcam (Cambridge, Mass.). Cdh1 and cyclin E antibodies, curcumin and vanillylidenacetone (half-curcumin) were purchased from Sigma-Aldrich (St. Louis, Mo.).

B. Cytotoxicity Assay

Lactate dehydrogenase (LDH) levels as a measure of cell death were determined using the Non-radioactive Cytotoxicity kit (Promega, Madison, Wis.) according to manufacturer's instructions. LDH release was determined from curcumin-treated and untreated control cells grown on 24-well plates by collecting growth medium. Cell debris was removed by centrifugation. Viable cell LDH was collected from cells lysed by freezing for 15 minutes at −70° C. followed by thawing at 37° C. The medium was collected and cleared from cell debris by centrifugation. The relative release of LDH was determined as the ratio of released LDH versus total LDH from viable cells.

C. Immunoblotting, Immunoprecipitations, and λ-Phosphatase Treatment

Cell lysates were prepared in a buffer containing 20 mM Tris (pH 7.5), 150 mM NaCl, 1 mM EDTA, 1 mM EGTA, 0.1% Triton X-100, 2.5 mM sodium pyrophosphate, 1 mM β-glycerol phosphate, 1 mM sodium vanadate, 1 mM phenylmethylsulfonyl fluoride and 5 µg/ml of antipapain, leupeptin and pepstatin (protease inhibitor cocktail). Protein concentrations were determined by the Dc protein assay (Bio-Rad, Hercules, Calif.). Equal amounts of protein were resolved by SDS-PAGE and transferred to nitrocellulose. The membranes were blocked in 5% non-fat milk in Tris-buffered saline with 0.1% Tween-2.0 (TBST). Primary antibodies diluted in 5% bovine serum albumin/TBST were incubated overnight at 4° C. and HRP-conjugated secondary antibodies in 5% non-fat milk/TBST for 2 hours at room temperature. Protein bands were visualized by Enhanced Chemiluminescence Plus (GE Healthcare, Piscataway, N.J.).

For immunoprecipitation, cells were lysed at 4° C. for 30 min in a buffer of 50 mM HEPES, pH 7.4, 150 mM NaCl 0.5% NP-40, 1 mM EDTA, 1 mM $Na_3VO_4$, 1 mM aprotinin, 1 mM leupeptin and 1 mM PMSF. Equal amounts of protein (from 0.5 to 2 mg) were incubated with Cdc27 antibody for 4 hours at 4° C. followed by protein G-Sepharose (GE Healthcare) for 2 hours, washed extensively, and analyzed by immunoblotting with indicated antibodies. For λ-phosphatase treatment, Cdc27 was immunoprecipitated as above except that phosphatase and protease inhibitors were omitted and then incubated with λ-☐phosphatase according to the manufacturer's protocol (New England Biolabs, Ipswich, Mass.).

D. Cell Cycle Analysis

Interphase DAOY cells were treated with curcumin for indicated times, trypsinized, and fixed in cold 70% ethanol. DNA was stained with 100 µg/ml propidium iodide (PI) in hypotonic citrate buffer with 20 µg/ml ribonuclease A. Stained nuclei were analyzed for DNA-PI fluorescence using an Accuri C6 flow cytometer (Accuri Cytometers Inc., Ann Arbor, Mich.). Resulting DNA distributions for sub G0/G1, G0/G1, S and G2/M phase of the cell cycle were analyzed with CFlow plus software (Accuri Cytometers Inc).

For analysis of cell cycle profiles after mitotic block, cells were synchronized with 2 mM thymidine for 24 hours. The block was released for 3 hours and cells were arrested in prometaphase with 100 nM nocodazole for 12 hours. For G1/S arrest, cells were synchronized for 18 hours with 2 mM thymidine, released for 9 hours, followed by a second thymidine arrest for 18 hours. The block was then released in the presence of DMSO or curcumin as indicated and the cells were processed as described above.

E. In Vitro APC Assay

In vitro APC assays were performed as described (Rajasekaran et al., *Molecular Cancer Therapeutics* 7(7); 2142-2151 (2008) using an in vitro transcribed and translated N-terminal fragment of cyclin $B_1$ (cyclin $B_1$-$N_{1-102}$) as substrate, $^{35}S$-methionine labeled cyclin $B_1$-$N_{1-102}$ was obtained using the TNT quick-coupled Transcription/Translation system (Promega, Madison, Wis.). Cell pellets of control and curcumin-treated DAOY cells were snap frozen in liquid nitrogen. The cell pellets were resuspended in an ice-cold hypotonic buffer (20 mM Hepes pH 7.6, 20 mM NaF, 1.5 mM $MgCl_2$, 1 mM DTT, 5 mM KCl, 20 mM β-glycerophosphate, 250 µM $NaVO_3$, 1 mM PMSF, and EDTA-free protease inhibitors) and incubated for 30 minutes on ice. The lysates were briefly homogenized and cleared by a 1 hour centrifugation at 13,000 rpm in a micro centrifuge. For the assay, 30 µg of total protein were added to reaction buffer containing 20 mM Tris pH 7.5, 20 mM NaCl, 5 mM MgCl$_2$, 5 mM ATP-γ-S, 20 µg/ml MG-132, 0.5 µg UbcH10, 20 µM ubiquitin, 1 µm ubiquitin aldehyde, protease inhibitor, and 2 µl of in vitro translated $^{35}$S-cyclin B$_1$-N$_{1-102}$ and incubated at 37° C. for 60 minutes. The reactions were stopped by adding sample buffer and proteins were separated by SDS-PAGE on a 4-15% gradient gel. To visualize the bands, the gel was incubated and enhanced with salicylate, dried, and then subjected to autoradiography.

F. Immobilization of Curcumin on Epoxy-Activated Sepharose 6B

Curcumin was coupled to epoxy-activated Sepharose 6B as previously described by Conboy et al. *Biochemical Pharmacology* 77(7): 1254-1265 (2009). Briefly, 20 mM curcumin dissolved in coupling buffer (50% dimethylformamide/0.1 M Na$_2$CO$_3$/10 mM NaOH) was incubated with swollen epoxy-activated Sepharose 6B beads overnight at 30° C. After washing, unoccupied binding sites were blocked with 1 M ethanolamine by overnight incubation. Low (0.1 M acetate buffer, pH 4) and high (0.1 M Tris-HCl, pH 8, 0.5 M NaCl) pH buffers were used each three times to wash and equilibrate the beads. Control beads were prepared in parallel with curcumin-coupled beads but curcumin was omitted. DAOY cell lysates were prepared in a lysis buffer of 100 mM HEPES, pH 7.6, 300 mM NaCl, 0.1% Triton X-100, 2 mM EDTA, 2 mM EGTA supplemented with phosphatase and protease inhibitors. 500 µg of protein was mixed with 20 µl of curcumin-coupled Sepharose beads and incubated for 3 hours at 4° C. After washing bound proteins were eluted with 1×SDS-PAGE sample buffer and processed for immunoblotting.

G. In Vivo Studies

Tumors of control and curcumin-treated mice were harvested exactly as described (Lee et al., 2011, *BMC Cancer* 11:144). Animal experiments were performed according to the NIH Guide for the Care and Use of Experimental Animals and approved by our Institutional Animal Care and Use Committee.

H. Statistical Analysis

Data are presented as mean±SD unless otherwise indicated. The differences between means of two groups were analyzed by a two-tailed unpaired Student's test. When required, P values are stated in the figure legends.

Example 1

Curcumin-Induced Cell Cycle Arrest in Medulloblastoma Cells

A. Cell Cycle Analysis Protocols

Interphase DAOY medulloblastoma cells were treated with curcumin for indicated times, trypsinized, and fixed in cold 70% ethanol. DNA was stained with 100 µg/ml propidium iodide (PI) in hypotonic citrate buffer with 20 µg/ml ribonuclease A. Stained nuclei were analyzed for DNA-PI fluorescence using an Accuri C6 flow cytometer (Accuri Cytometers Inc., Ann Arbor, Mich.). Resulting DNA distributions for sub G0/G1, G0/G1, S and G2/M phase of the cell cycle were analyzed with CFlow plus software (Accuri Cytometers. Inc).

For analysis of cell cycle profiles after mitotic block, cells were synchronized with 2 mM thymidine for 24 hours. The block was released for 3 hours and cells were arrested in prometaphase with 100 nM nocodazole for 12 hours. For G1/S arrest, cells were synchronized for 18 hours with 2 mM thymidine, released for 9 hours, followed by a second thymidine arrest for 18 hours. The block was then released in the presence of DMSO or curcumin as indicated and the cells were processed as described above. The cell-cycle dependent cytotoxicity of curcumin was measured by the LDH assay described in Materials and Methods. The data from these cell cycle studies are the mean±SEM of three independent experiments.

B. Results

DAOY medulloblastoma cells were arrested in G1/S block and the block was released in the presence of 0, 10 or 20 µM curcumin. At 0, 4, 8, 12, 16 and 20 hours, cell cycle progression was analyzed by flow cytometry. The DAOY medulloblastoma cells released from a G1/S block in the presence of curcumin progressed much slower through the cell cycle compared to vehicle-treated control cells (FIG. 1A and Table 1). While most control cells reached G2/M 8-12 hours after release and almost 100% of G1/S blocked cells re-entered G0/G1 after 16 hours, cells released in the presence of 10 and 20 µM curcumin reached G2/M only after 12-16 and 16-20 hours, respectively. In addition, 56.9% of the cells released in the presence of 20 µM curcumin had not re-entered G0/G1 even 20 hours after removal of the thymidine block. However, no sub-G0/G1 signal, was detected indicating that although the cells were delayed in mitosis they did not undergo apoptosis within this time frame (FIG. 1A). Together these data suggest that the sensitivity of DAOY cells to curcumin-induced cell-death may be cell-cycle dependent.

TABLE 1

| Hr | G0/G1 | S | G2/M |
|---|---|---|---|
| | 0 µM Curcumin | | |
| 0 | 48.15 ± 0.32 | 18.89 ± 2.17 | 32.96 ± 1.97 |
| 4 | 37.76 ± 5.39 | 33.22 ± 2.40 | 29.04 ± 3.09 |
| 8 | 26.40 ± 6.49 | 33.06 ± 3.30 | 40.54 ± 8.15 |
| 12 | 37.00 ± 6.79 | 23.61 ± 3.60 | 39.38 ± 10.23 |
| 16 | 49.50 ± 3.77 | 23.06 ± 3.87 | 27.41 ± 4.35 |
| 20 | 48.34 ± 2.28 | 21.17 ± 0.89 | 24.52 ± 1.51 |
| | 10 µM Curcumin | | |
| 0 | 48.15 ± 0.32 | 18.89 ± 2.17 | 32.96 ± 1.97 |
| 4 | 41.92 ± 5.16 | 32.13 ± 2.64 | 25.88 ± 3.55 |
| 8 | 24.94 ± 4.83 | 39.71 ± 4.45 | 35.33 ± 5.04 |
| 12 | 32.40 ± 8.28 | 22.71 ± 3.49 | 44.92 ± 11.40 |
| 16 | 42.40 ± 6.35 | 22.75 ± 3.63 | 34.85 ± 9.11 |
| 20 | 46.46 ± 2.96 | 23.66 ± 4.26 | 29.88 ± 3.86 |
| | 20 µM Curcumin | | |
| 0 | 48.15 ± 0.32 | 18.89 ± 2.17 | 32.96 ± 1.97 |
| 4 | 40.18 ± 5.31 | 31.55 ± 3.94 | 28.33 ± 1.56 |
| 8 | 31.66 ± 3.64 | 36.76 ± 2.49 | 31.58 ± 2.35 |
| 12 | 21.69 ± 2.77 | 37.87 ± 3.29 | 40.44 ± 3.95 |
| 16 | 20.99 ± 2.17 | 30.34 ± 4.57 | 48.68 ± 5.04 |
| 20 | 27.44 ± 4.69 | 29.53 ± 0.59 | 43.06 ± 5.04 |

Figure 1B:
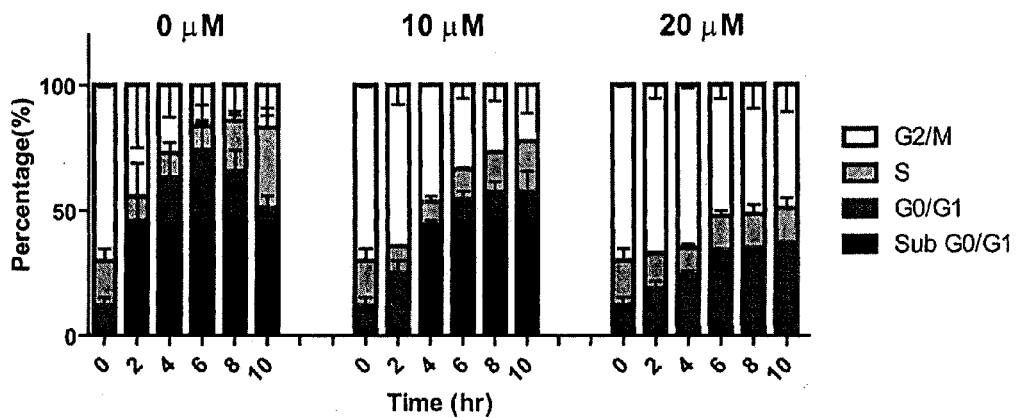

In another experiment, DAOY cells were mitotically arrested in G2/M by thymidine/nocodazole treatment and released from their block in the presence or absence of curcumin (0, 10 or 20 µM curcumin). Cell cycle profiles were determined at 0, 4, 8, 12, 16 and 20 hours. The results are shown in FIG. 1B and Table 2. While 70.2% of the cells were blocked in G2/M, 36.8% of control cells exited mitosis within two hours of release and by 6 hours 76.9% had exited G2/M. In the presence of 10 µM curcumin mitotic exit was significantly delayed and after two and six hours 91.5% and 47.7% of the cells, respectively, remained in G2/M. This effect was much more pronounced in the presence of 20 µM curcumin when after 10 hours of release still 69.8% of the cells were found in G2/M. At the same time a significant amount of cells was in the sub-G0/G1 fraction suggesting that curcumin-induced delay from G2/M exit may commit the cells to undergo apoptosis. Together with FIG. 1A and Table 1, these data suggest that the sensitivity of DAOY cells to curcumin-induced cell-death is cell-cycle dependent.

TABLE 2

| Hr | Sub G0/G1 | G0/G1 | S | G2/M |
|---|---|---|---|---|
| | | 0 μM Curcumin | | |
| 0 | 4.80 ± 2.40 | 7.38 ± 3.12 | 17.68 ± 4.78 | 70.15 ± 0.75 |
| 2 | 6.91 ± 2.21 | 39.08 ± 22.88 | 9.67 ± 0.03 | 44.33 ± 25.07 |
| 4 | 6.18 ± 0.62 | 57.10 ± 13.80 | 9.62 ± 0.48 | 27.10 ± 12.70 |
| 6 | 7.31 ± 0.59 | 67.03 ± 17.73 | 9.46 ± 2.34 | 16.20 ± 14.80 |
| 8 | 6.72 ± 0.12 | 59.00 ± 8.10 | 20.02 ± 2.22 | 14.31 ± 10.49 |
| 10 | 5.52 ± 0.38 | 45.83 ± 4.63 | 31.69 ± 7.89 | 17.02 ± 12.18 |
| | | 10 μM Curcumin | | |
| 0 | 4.80 ± 2.40 | 7.38 ± 3.12 | 17.68 ± 4.78 | 70.15 ± 0.75 |
| 2 | 8.21 ± 2.91 | 16.87 ± 4.87 | 10.76 ± 0.04 | 64.16 ± 7.74 |
| 4 | 8.57 ± 0.13 | 35.54 ± 1.94 | 9.47 ± 2.03 | 46.47 ± 0.17 |
| 6 | 10.57 ± 2.67 | 43.93 ± 3.13 | 12.07 ± 0.53 | 33.43 ± 5.27 |
| 8 | 9.99 ± 2.79 | 47.60 ± 4.00 | 15.54 ± 0.56 | 26.86 ± 6.24 |
| 10 | 8.85 ± 3.45 | 48.68 ± 8.18 | 19.88 ± 0.32 | 22.65 ± 11.35 |
| | | 20 μM Curcumin | | |
| 0 | 4.80 ± 2.40 | 7.38 ± 3.12 | 17.68 ± 4.76 | 70.15 ± 0.75 |
| 2 | 7.42 ± 2.92 | 11.51 ± 2.81 | 13.86 ± 0.34 | 67.21 ± 5.39 |
| 4 | 7.46 ± 1.36 | 16.77 ± 1.63 | 10.77 ± 1.57 | 65.00 ± 1.30 |
| 6 | 11.67 ± 4.37 | 22.09 ± 0.81 | 14.02 ± 2.02 | 52.27 ± 5.63 |
| 8 | 10.85 ± 5.55 | 24.20 ± 0.30 | 13.45 ± 3.65 | 51.55 ± 9.55 |
| 10 | 11.67 ± 6.07 | 25.15 ± 0.85 | 14.22 ± 4.02 | 48.95 ± 10.95 |

Figure 1C:
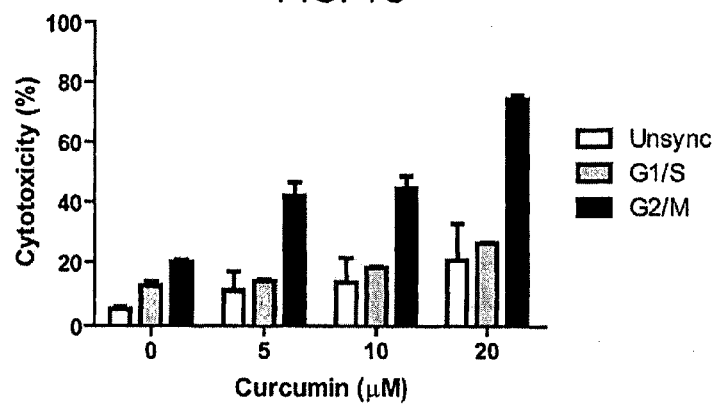

In another experiment, unsynchronized cells were treated with 0, 10 or 20 μM curcumin for 12 hours. The results are shown in FIG. 1C. DAOY cells treated with 20 μM curcumin in G2/M were 3-fold more sensitive to curcumin-induced cell death than cells arrested in either G1/S or unsynchronized control cells. Thus, curcumin may affect the function of proteins directly involved in G2/M progression to ultimately induce cell death.

Example 2

Curcumin-Induced Effects on APC/C and Other Cell Cycle-Related Proteins

Figure 2C:
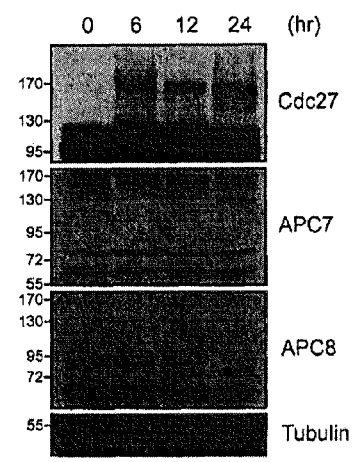

To test whether curcumin affects, known regulators of mitosis, the expression of various cell cycle proteins in control and curcumin-treated DAOY cells was investigated.
A. Assay Protocol
Cell lysates were prepared in a buffer containing 20 mM Iris (pH 7.5), 150 mM NaCl, 1 mM EDTA, 1 mM EGTA, 0.1% Triton X-100, 2.5 mM sodium pyrophosphate, 1 mM β-glycerol phosphate, 1 mM sodium vanadate, 1 mM phenylmethylsulfonyl fluoride and 5 μg/ml of antipapain, leupeptin and pepstatin (protease inhibitor cocktail). Protein concentrations were determined by the Dc protein assay (Bio-Rad, Hercules, Calif.). Equal amounts of protein were resolved by SDS-PAGE and transferred to nitrocellulose. The membranes were blocked in 5% non-fat milk in Tris-buffered saline with 0.1% Tween-20 (TBST). Primary antibodies diluted in 5% bovine serum albumin/TBST were incubated overnight at 4° C. and HRP-conjugated secondary antibodies in 5% non-fat milk/TBST for 2 hours at room temperature. Protein bands were visualized by Enhanced Chemiluminescence Plus (GE Healthcare, Piscataway, N.J.).
B. Results
The curcumin-induced effects on APC/C and other cell cycle related proteins are shown in FIGS. 2A through 2C. FIG. 2A shows the expression of the APC/C subunit APC2, the APC/C co-activator p55Cdc20 and cyclins A and E in control and curcumin-treated DAOY cells as determined by immunoblotting. GAPDH levels are included to ensure equal loading. FIG. 2B is an immunoblot of the APC/C subunit Cdc27 showing a curcumin-induced shift in molecular weight (arrows). Because of differences in band intensity the same immunoblot is shown with two different exposures. Arrowhead and asterisk indicate the non- and phosphorylated bands of Cdc27, respectively. FIG. 2C is a comparison of the molecular weight shift by curcumin between Cdc27 and other APC components. Tubulin was used for equal loading control.

No noticeable changes were observed in cyclin A and E that are major players in S-phase and G1/S transition, respectively. Also, the levels of APC2, an APC/C subunit essential for ubiquitination, or the APC/C co-activator p55Cdc20, were comparable in control and curcumin-treated cells (FIG. 2A). Immunoblots of Cdc27 revealed a high molecular weight (MW) band in curcumin-treated cells that was approximately double the MW of Cdc27 and its intensity increased with increasing curcumin concentrations (FIG. 2B). This effect appeared to be specific for Cdc27, since a molecular weight shift of APC7 or APC8 was not detectable. Both APC7 and APC8, like Cdc27/APC3, have tetratricopeptide repeat (TPR) domains (FIG. 2C).

Example 3

Curcumin Binding to the Phosphorylated Form of Cdc27

Figure 3A:
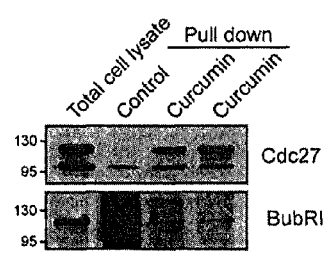
FIGS. 3A, 3B and 3C demonstrate that curcumin binds to APC3/Cdc27, specifically the phosphorylated form of Cdc27.
Figure 3B:
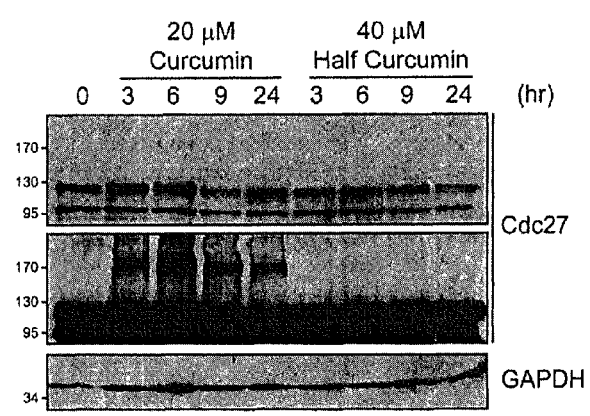
Figure 3C:
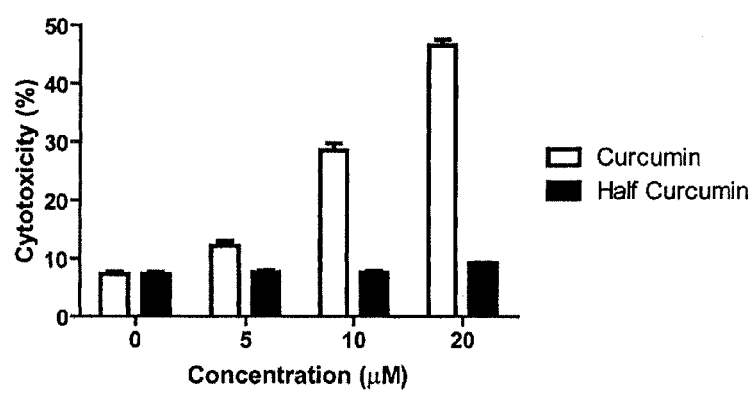

The following series of experiments demonstrates that curcumin binds to the phosphorylated form of Cdc27.
DAOY cell lysates were incubated with curcumin-bound Sepharose beads and then subjected to SDS-PAGE and immunoblotting with Cdc27. A BubR1 immunoblot was included as control for non-specific binding. The results are shown in FIG. 3A. In another experiment, DAOY cell lysates were then incubated with either curcumin or half-curcumin (dehydrozingerone, DHZ, 4-(4-hydroxy-3-methoxyphenyl)-3-buten-2-one) for 0, 3, 6, 9 or 24 hours. The cell lysates were separated by SDS-PAGE and immunoblotted for Cdc27. The results are shown in FIG. 3B. The middle panel in FIG. 3B shows a longer exposure of the same blot in the upper panel. Decreased levels of non-crosslinked Cdc27 were observed in non-curcumin-treated cells (FIG. 3B). In another experiment, LDH release was determined as a measure of cytotoxicity of curcumin and half-curcumin in DAOY cells treated for 16 hours. The results are shown in FIG. 3C. Data represent mean±SEM of three independent experiments.

The results show that curcumin-bound Sepharose beads from two independent preparations pulled down Cdc27 while it was barely detected with control beads (FIG. 3A). Curcumin appeared to have a higher affinity for the 130 kDa form of Cdc27 (FIG. 3A, upper band). This molecular weight is consistent with the phosphorylated form of Cdc27. In addition, half-curcumin which has only one β-diketone moiety and does not have cross-linking capacity, failed to induce the high molecular weight bands of Cdc27, indicating that curcumin induces the formation of Cdc27 dimers (FIG. 36). Half-curcumin also failed to induce cell death in DAOY cells (FIG. 3C) indicating that cross-linking of Cdc27 may be an essential step in curcumin-induced apoptosis in these cells (FIG. 3C).

Example 4

Reduction of APC3/Cdc27 Levels in Smo/Smo Mouse Tumors

Figure 4:
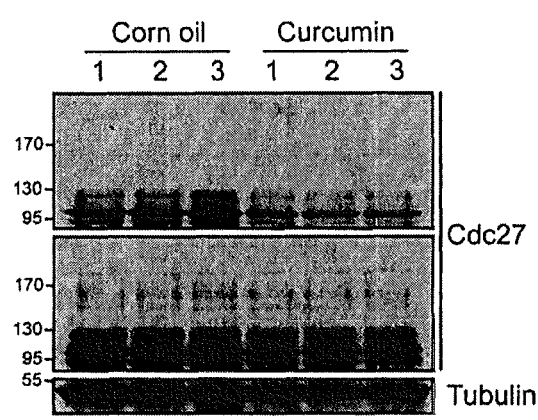
FIG. 4 shows an immunoblot of Cdc27 levels in medulloblastoma samples obtained from Smo/Smo mice treated with curcumin or corn oil. Tubulin was shown for equal loading.

Medulloblastoma samples from Smo/Smo mice treated with curcumin or corn oil were harvested as described as described (Lee et al., 2011, *BMC Cancer* 11:144). Cdc27 levels in the Smo/Smo mouse tumors were determined by immunoblot of Cdc27. The results are shown in FIG. 4. Tubulin is shown for equal loading. The Cdc27 levels were reduced (FIG. 4) when compared with control mice.

Example 5

Cdc27 Phosphorylation Sensitizes Tumor Cells to Curcumin

The following series of experiments demonstrates that Cdc27 phosphorylation sensitizes tumor cells to curcumin.

Figure 5A:
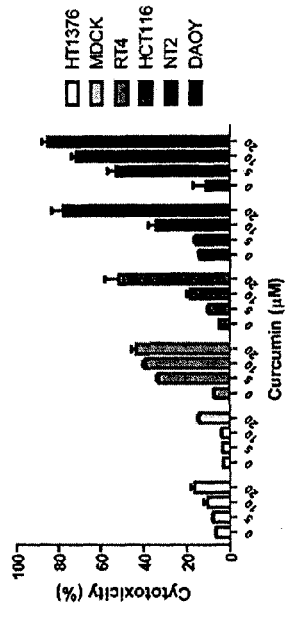
FIGS. 5A, 5B, 5C and 5D demonstrate that Cdc27 phosphorylated sensitizes tumor cells to curcumin.

The cell lines DAOY, NT2, D283 Med, D341 Med (brain); HCT116 (colon); HT1376, RT4 (bladder); MDCK (kidney) were screened for Cdc27 phosphorylation by immunoblot of Cdc27. The results are shown in FIG. 5A. The arrow indicates the band corresponding to phosphorylated Cdc27 and arrowhead shows unphosphorylated Cdc27. Actin immunoblot is shown as loading control.

Figure 5B:
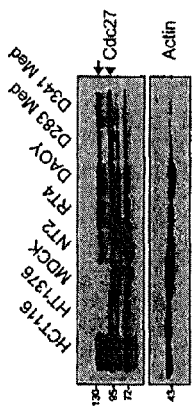

FIG. 5B shows the results of a Cdc27 immunoblot of the cells lines after treatment with 20 µM curcumin for 0, 4, 8, and 24 hours. Arrows indicate crosslinked Cdc27, while arrowheads show phosphorylated Cdc27. Equal amounts of protein were used as shown by actin immunoblot. Only in cell lines with the phosphorylated form of Cdc27 was curcumin able to crosslink Cdc27 (FIG. 5B) further confirming that curcumin dimerizes preferentially phosphorylated Cdc27.

Figure 5C:
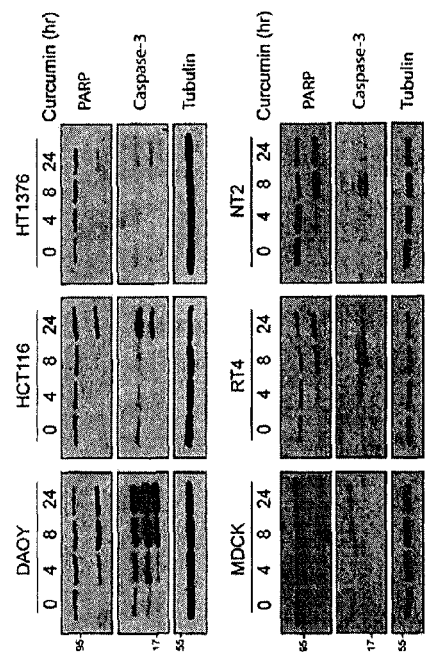

Six of the above cell lines with, high (DAOY, HCT116), intermediate (RT4, NT2) and low (HT1376, MDCK) levels of phosphorylated Cdc27 were tested for their sensitivity to curcumin-induced cell death. Cytotoxicity of curcumin was determined by LDH release assay. LDH release was determined after 24 hours of exposure to curcumin at 0, 5, 10 and 20 µM concentrations. The data shown in FIG. 5C represent the mean±SEM of three independent experiments. DAOY cells were most sensitive to curcumin-induced apoptosis while MDCK and HT1376 cells were almost unaffected. See FIGS. 5C and 5D; and FIG. 7. The data indicate that curcumin preferentially induces apoptosis in cells with high levels of Cdc27 phosphorylation.

Figure 5D:
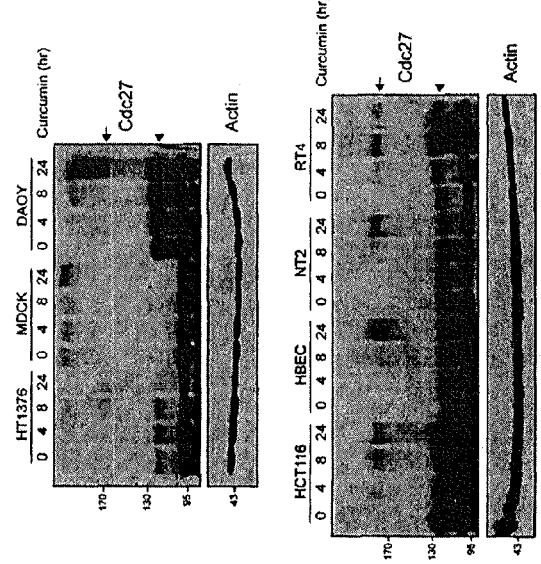

Cleaved PARP and caspase-3 are indicators of apoptosis. The same cell lines were subject to immunoblots of cleaved PARP and caspase-3 as indicators of apoptosis upon exposure to 20 µM curcumin. The data are shown in FIG. 5D. Tubulin immunoblot was carried out to ensure equal amounts of protein being used for analysis.

Example 6

Expression of Phosphorylated Cdc27 in DAOY Medulloblastoma Cells

Immunoprecipitated Cdc27 from DAOY cells was incubated with or without λ-phosphatase for indicated time points and then resolved in SDS-PAGE for Western blotting. The results shown in FIG. 6 confirm that phosphorylated form of Cdc27 is present. The arrowhead in FIG. 6 indicates non-phosphorylated Cdc27. The asterisk indicates IgG of input antibodies.

Example 7

Curcumin Blockade of Mitotic Progression in Cell Lines with Phosphorylated Cdc27

Figure 7A:
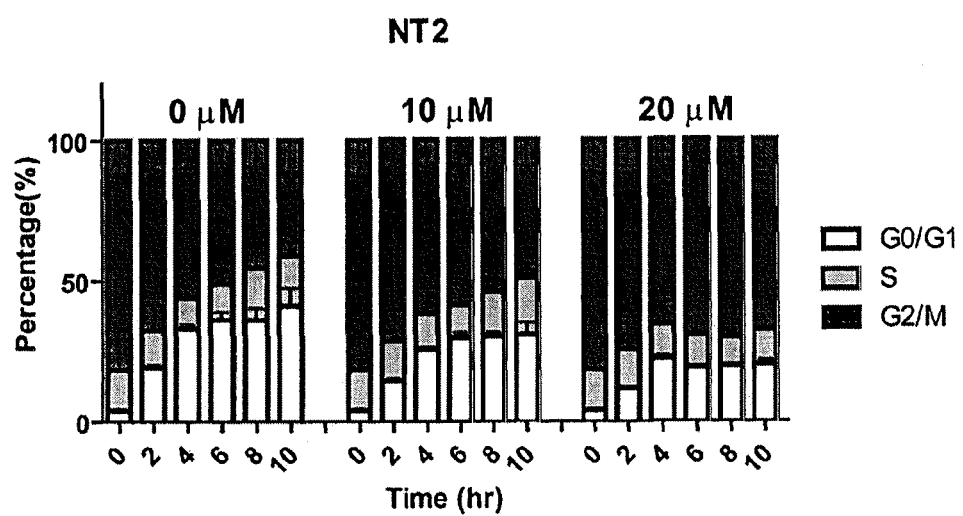
FIGS. 7A and 7B show the cell-cycle progression of NT2 (FIG. 7A) and MDCK (FIG. 7B) cells treated with curcumin. Cells were arrested with thymidine/nocodazole, and washed and then released from mitotic block with different concentrations of curcumin for the indicated time points. DNA contents were analyzed for cell cycle progression. Data are expressed as mean±SEM of three independent experiments.
Figure 7B:
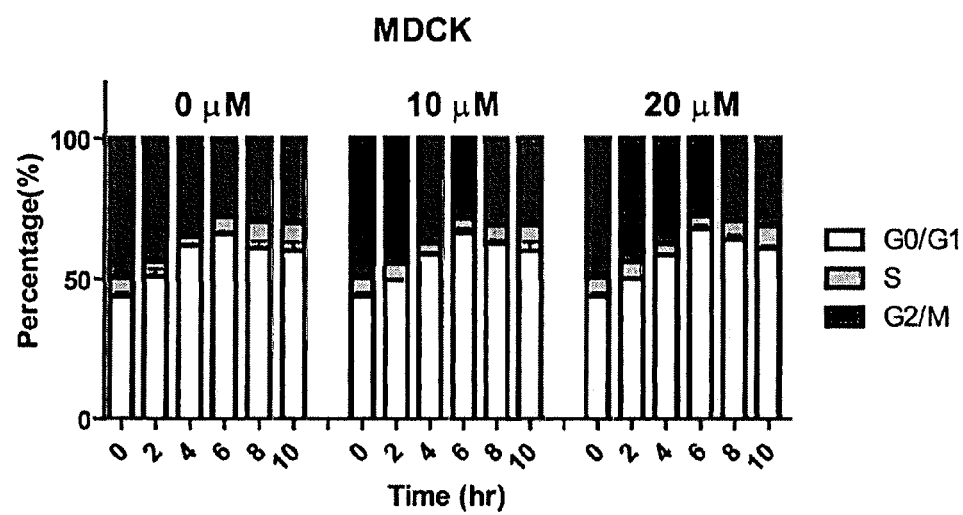

NT2 and MDCK cells were arrested with thymidine/nocodazole treatment. Cells were washed and then released from mitotic block with different concentrations of curcumin for indicated time points. DNA contents were analyzed for cell cycle progression. The data shown in FIG. 7 are expressed as mean±SEM of three independent experiments. The data show that curcumin selectively blocks mitotic progression in different cell lines with phosphorylated APC3/Cdc27.

Example 8

Curcumin Inhibition of the Activity of the Anaphase Promoting Complex APC/C

In vitro APC assays were performed to test whether cross-linking of Cdc27 by curcumin compromises APC/C activity. The assay conditions were, as described in part E, "In vitro APC assay", in "Materials and Methods", above.

To test whether cross-linking of Cdc27 by curcumin compromises APC/C activity, DAOY cells were arrested in G2/M and released the block in the absence or presence of curcumin. Accordingly, DAOY cells were released from thymidine/nocodazole block in the presence of 0, 20 and 40 µM curcumin for the time points indicated in FIG. 8A (0.5, 1, 1.5, 2 and 4 hours). Cell lysates were subjected to immunoblotting with antibodies to Cdc27, Cyclin B1, cyclin D1 or GADPH as indicated in FIG. 8A. The arrow indicates phosphorylated Cdc27, while the arrowhead shows unphosphorylated Cdc27. In a separate experiment, mitotically arrested DAOY cells were released with 20 or 40 µM concentrations of curcumin for 2 and 4 hours, respectively, and blotted with antibodies to cyclin D1, Securin, APC2 or p55 Cdc20.

Release of the mitotic block in DMSO-treated control cells resulted in the dephosphorylation of Cdc27 over time which was not observed in curcumin-treated cells (FIG. 8A). In addition, decreases in the cyclin B1 and securin levels that are a prerequisite for mitotic exit were not found in curcumin-treated cells but were readily observed in control cells (FIGS. 8A, 8B). In contest, no significant differences were found in the levels of the core APC/C subunit APC2, the APC/C coactivator p55Cdc20 or cyclin D1 in control and curcumin-treated cells (FIGS. 8A, B). Together, these data indicate that curcumin may directly affect the function of the APC/C.

Proper APC/C function requires co-activator proteins such as Cdc20 or Cdh1 that may facilitate the recruitment of substrates. Accordingly, DAOY cells were synchronized by double thymidine arrest and then incubated with curcumin for 8 hours. Cell lysates were subjected to immunoprecipitation with anti-Cdc27 antibodies. Immunoprecipitated proteins were immunoblotted with antibodies to APC2, APC8, p55 Cdc20 or Cdh1. Immunoblots of total cell lysates are shown to ensure equal loading. The co-immunoprecipitation analysis that in DAOY cells released from a G2/M block in the presence of curcumin showed that p55Cdc20 association with Cdc27 was dramatically reduced compared to control cells, while the Cdc27 association with the APC/C subunits APC2 and APC8 was not affected (FIG. 8C). Under the experimental conditions used, Cdh1 was not found to be associating with Cdc27 (FIG. 8C).

Whether curcumin affects the activity of APC/C was tested using an in vitro APC assay that monitors APC's ubiquitin ligase activity on cyclin B as described earlier (Rajasekaran et al., *Molecular Cancer Therapeutics* 7(7); 2142-2151 (2008). The cells were arrested in G2/M and released from the block in the presence of either DMSO, or 20 μM or 40 μM curcumin for 1 or 1 or 2 hours. APC/C activity was determined as described in Materials and Methods.

Figure 8D:
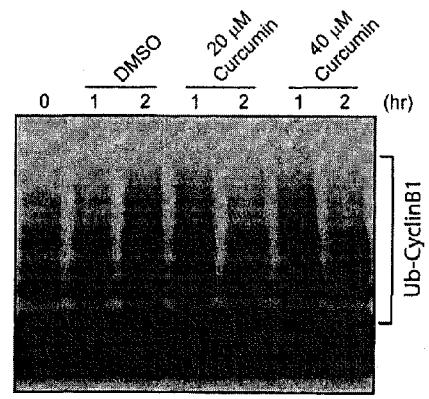

Compared to cells blocked at G2/M (FIG. 8D), a gradual increase of APC activity upon block release in control cells was observed, indicating that these cells were exiting mitosis. In contrast, in curcumin-treated cells the APC activity was reduced two hours after block release when compared to cells after one hour of release indicating that curcumin inhibits APC activity directly.

Together these data indicate that cross-linking of Cdc27 by curcumin reduces its association with its co-activator p55Cdc20, thus Inhibiting APC activity.

Example 9

Curcumin Induces Acetylated Tubulin Accumulation

The cell lines HT1376, MDCK, NT2, HCT116; DAOY and RT4 were incubated with 20 μM curcumin for 0, 4, 8 and 24 hours. Accumulation of acetylated tubulin was assayed. The results are shown in FIG. 9. In cells with low levels of phosphorylated Cdc27 in which curcumin failed to cross-link Cdc27 and that were less sensitive to curcumin treatment, curcumin-induced tubulin acetylation was also reduced (FIG. 9). Thus, loss of Cdc27 function or p55Cdc20 association with Cdc27 may be linked to increased tubulin acetylation in curcumin-treated cells.

The disclosures of each and every patent, patent application, publication and GenBank record cited herein are hereby incorporated herein by reference in their entirety.

One skilled in the art will readily appreciate that the present invention is well adapted to carry out the objects and obtain the ends and advantages mentioned, as well as those inherent therein. While the invention has been disclosed with reference to specific embodiments, it is apparent that other embodiments and variations of this invention may be devised by others skilled in the art without departing from the true spirit and scope used in the practice of the invention. The appended claims are intended to be construed to include all such embodiments and equivalent variations.

The invention claimed is:

1. A method of identifying a patient with cancer who is most likely to benefit from treatment with an agent that binds phosphorylated Cdc27, the method comprising:
(a) obtaining a sample of cancer cells from the patient;
(b) determining whether the sample comprises cancer cells that contain phosphorylated Cdc27; and
(c) identifying the patient as one most likely to benefit from treatment with an agent that binds phosphorylated Cdc27, if the cancer cells comprise phosphorylated Cdc27.

2. The method according to claim 1, wherein the agent that binds phosphorylated Cdc27 crosslinks said phosphorylated Cdc27, and the method is for identifying the patient as one most likely to benefit from treatment with an agent that crosslinks phosphorylated Cdc27, if the cancer cells comprise phosphorylated Cdc27.

3. A method of predicting whether a cancer patient is afflicted with a tumor that will respond effectively to treatment with an agent that binds phosphorylated Cdc27, the method comprising:
(a) obtaining a sample of the patient's tumor;
(b) determining whether the sample comprises tumor cells that contain phosphorylated Cdc27; and
(c) predicting that the tumor will respond effectively to treatment with an agent that binds phosphorylated Cdc27, if tumor cells of the sample contain phosphorylated Cdc27.

4. The method according to claim 3, wherein the agent that binds phosphorylated Cdc27 crosslinks said phosphorylated Cdc27, and the method is for predicting that the tumor will respond effectively to treatment with an agent that crosslinks phosphorylated Cdc27, if tumor cells of the sample contain phosphorylated Cdc27.

5. A method of assessing whether a cancer patient afflicted with a tumor who is undergoing treatment with an agent that binds phosphorylated Cdc27 will continue to respond effectively to said treatment, the method comprising:
(a) obtaining a sample of the patient's tumor;
(b) determining whether the sample comprises tumor cells that contain phosphorylated Cdc27; and
(c) predicting that the tumor will continue to respond effectively to treatment with said agent that binds phosphorylated Cdc27, if tumor cells of the sample contain phosphorylated Cdc27.

6. The method according to claim 5, wherein the agent that binds phosphorylated Cdc27 crosslinks said phosphorylated Cdc27, and the method is for predicting that the tumor will continue to respond effectively to treatment with said agent that crosslinks phosphorylated Cdc27, if tumor cells of the sample contain phosphorylated Cdc27.

7. The method according to any of claim 1, 3, 4, 5 or 6 wherein the agent comprises curcumin.

8. A method of identifying a patient with cancer who is most likely to benefit from treatment with curcumin, the method comprising:
(a) obtaining a sample of cancer cells from the patient;
(b) determining whether the sample comprises cancer cells that contain phosphorylated Cdc27; and
(c) identifying the patient as one most likely to benefit from treatment with curcumin, if the cancer cells comprise phosphorylated Cdc27.

9. A method of predicting whether a cancer patient is afflicted with a tumor that will respond effectively to treatment with curcumin, the method comprising:
(a) obtaining a sample of the patient's tumor;
(b) determining whether the sample comprises tumor cells that contain phosphorylated Cdc27; and
(c) predicting that the tumor will respond effectively to treatment with curcumin, if tumor cells of the sample contain phosphorylated Cdc27.

10. The method according to any of claim 1, 3, 4, 5 or 6 wherein the patient is afflicted with leukemia, lymphoma, multiple myeloma, gastrointestinal cancer; bladder cancer; kidney cancer; prostate cancer; breast cancer; cervical cancer; ovarian cancer; lung cancer; melanoma; brain cancer; or combination thereof.

11. The method according to claim 8 or 9 wherein the patient is afflicted with leukemia, lymphoma, multiple myeloma, gastrointestinal cancer; bladder cancer; kidney cancer; prostate cancer; breast cancer; cervical cancer; ovarian cancer; lung cancer; melanoma; brain cancer; or combination thereof.

12. A method of treating cancer in a patient, comprising:
(a) determining the patient's likely responsiveness to an agent that binds phosphorylated Cdc27 by:
(i) obtaining a sample of cancer cells from the patient;
(ii) determining whether the cancer cells contain phosphorylated Cdc27; and (iii) identifying the patient as one most likely to benefit from treatment with an agent that binds phosphorylated Cdc27, if the cancer cells comprise phosphorylated Cdc27;
(b) administering to said patient a therapeutically effective amount of an agent that binds phosphorylated Cdc27, if the patient is determined to be likely responsive to said therapeutic agent.

13. A method of treating cancer in a patient, comprising:
(a) determining the patient's likely responsiveness to an agent that binds phosphorylated Cdc27 by:
  (i) obtaining a sample of cancer cells from the patient;
  (ii) determining whether the cancer cells contain phosphorylated Cdc27; and
  (iii) identifying the patient as one most likely to benefit from treatment with an agent that crosslinks phosphorylated Cdc27, if the cancer cells comprise phosphorylated Cdc27; and
(b) administering to said patient a therapeutically effective amount of an agent that crosslinks phosphorylated Cdc27, if the patient is determined to be likely responsive to said therapeutic agent.

14. The method according to claim 12 or 13 wherein the patient is afflicted with leukemia, lymphoma, multiple myeloma, gastrointestinal cancer; bladder cancer; kidney cancer; prostate cancer; breast cancer; cervical cancer; ovarian cancer; lung cancer; melanoma; brain cancer; or combination thereof.

15. The method according to claim 12 or 13 wherein the administered agent comprises curcumin or an analogue, derivative or prodrug thereof.

16. The method of any of claim 1, 3, 4, 5 or 6, wherein determining whether the sample comprises cells that contain phosphorylated Cdc27 comprises an assay that utilizes a binding agent that is specific for phosphorylated Cdc27.

17. The method of claim 8 or 9 wherein determining whether the sample comprises cells that contain phosphorylated Cdc27 comprises an assay that utilizes a binding agent that is specific for phosphorylated Cdc27.

18. The method according to claim 10 wherein the patient is afflicted with medulloblastoma.

19. The method according to claim 11 wherein the patient is afflicted with medulloblastoma.

20. The method according to claim 14 wherein the patient is afflicted with medulloblastoma.

21. The method according to claim 15 wherein the administered agent comprises curcumin.

* * * * *